United States Patent
Kim et al.

(10) Patent No.: US 9,562,267 B2
(45) Date of Patent: Feb. 7, 2017

(54) STANDARD PLASMID FOR ASSAYING GENETICALLY MODIFIED ORGANISM, AND ANALYSIS METHOD AND ASSAY KIT USING SAME

(71) Applicant: KOREA RESEARCH INSTITUTE OF STANDARDS AND SCIENCE, Daejeon (KR)

(72) Inventors: Hyong Ha Kim, Daejeon (KR); Woo Jeong Kim, Daejeon (KR); Su Kyung Lee, Daejeon (KR); Jung Keun Suh, Daejeon (KR); Young Hye Seo, Daegu (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 14/942,241

(22) Filed: Nov. 16, 2015

(65) Prior Publication Data

US 2016/0138102 A1  May 19, 2016

Related U.S. Application Data

(63) Continuation-in-part of application No. PCT/KR2014/004402, filed on May 16, 2014.

(30) Foreign Application Priority Data

May 16, 2013 (KR) .......................... 10-2013-0056073

(51) Int. Cl.
| | | |
|---|---|---|
| *C12Q 1/68* | (2006.01) | |
| *C12N 15/82* | (2006.01) | |
| *C07K 14/42* | (2006.01) | |
| *C12N 9/10* | (2006.01) | |

(52) U.S. Cl.
CPC ............. *C12Q 1/6876* (2013.01); *C07K 14/42* (2013.01); *C12N 9/1092* (2013.01); *C12N 15/8275* (2013.01); *C12Q 1/6895* (2013.01); *C12Q 2600/13* (2013.01); *C12Q 2600/158* (2013.01); *C12Q 2600/166* (2013.01); *C12Y 205/01019* (2013.01)

(58) Field of Classification Search
None
See application file for complete search history.

(56) References Cited

FOREIGN PATENT DOCUMENTS

| CN | 102408090 A | * 4/2012 | ......... B81C 1/00063 |
|---|---|---|---|
| KR | 2003-0084184 A | 11/2003 | |
| KR | 10-2006-0011646 A | 2/2006 | |
| KR | 10-2011-0126306 A | 11/2011 | |

OTHER PUBLICATIONS

Online translation of CN 102409080 A to Cheng et al.*
GenBank Accession No. AF464188, Glycine max CP4EPSPS gene, complete cds, 2002.01.23, 2 pgs. total.
GenBank Accession No. K00821, Soybean lectin (Le1) gene, complete cds, Apr. 27, 1993, 3 pgs. total.
Report of the 2012 Asia & Pacific Nation Network (APNN) Meeting, The Association of Korean Woman Scientists and Engineers (KWSE), Jun. 13, 2012, 11 pgs. total.
2012 Annual Meeting, Korean Society of Food Science and Technology, Food Science & Communications, Jun. 13-15, 2012, 4 pgs. total.
48th Korean Society of Analytical Sciences, 2012, 6 pgs. total.
International Searching Authority, International Search Report of PCT/KR2014/004402, dated Jul. 11,2014. [PCT/ISA/210].

* cited by examiner

*Primary Examiner* — Jim Ketter
(74) *Attorney, Agent, or Firm* — Sughrue Mion, PLLC

(57) ABSTRACT

Provided is a standard plasmid for assaying a genetically modified plant, a method for quantitatively analyzing a target transgene within the genetically modified plant using the standard plasmid, and a kit for quantitatively analyzing the genetically modified plant including the standard plasmid, wherein the standard plasmid of the present invention is possible to be utilized for assaying a genome containing a 5-enoyl-4-pyruvylshikimate-3-phosphate synthase (EPSPS) gene or a cry1Ab gene, and in particular, significantly useful as a standard material capable of analyzing whether the genetically modified plant such as soybean RRS or GM maize MON810 is incorporated or an incorporation ratio thereof.

9 Claims, 21 Drawing Sheets

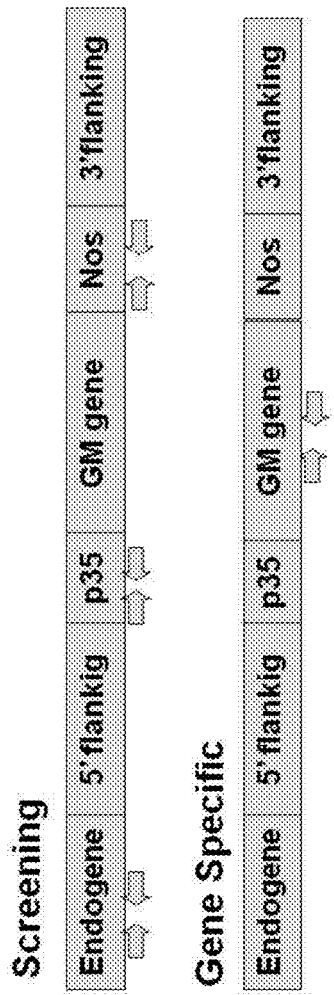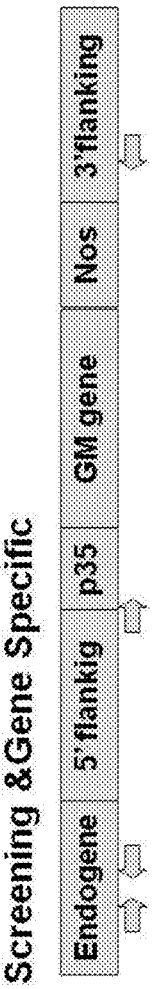
FIG. 17(a)
FIG. 17(b)

SEQUENCE LISTING

```
<160> NUMBER OF SEQ ID NOS: 25

<210> SEQ ID NO 1
<211> LENGTH: 1368
<212> TYPE: DNA
<213> ORGANISM: Artificial Sequence
<220> FEATURE:
<223> OTHER INFORMATION: Synthetic polynucleotide

<400> SEQUENCE: 1
atgcttcacg gtgcaagcag ccggcccgca accgcccgca aatcctctgg cctttccgga       60
accgtccgca ttcccggcga caagtcgatc tcccaccggt ccttcatgtt cggcggtctc      120
gcgagcggtg aaacgcgcat caccggcctt ctggaaggcg aggacgtcat caatacgggc      180
aaggccatgc aggccatggg cgccaggatc cgtaaggaag gcgacacctg gatcatcgat      240
ggcgtcggca atggcggcct cctggcgcct gaggcgccgc tcgatttcgg caatgccgcc      300
acgggctgcc gcctgaccat gggcctcgtc ggggtctacg atttcgacag caccttcatc      360
ggcgacgcct cgctcacaaa gcgcccgatg ggccgcgtgt tgaacccgct gcgcgaaatg      420
ggcgtgcagg tgaaatcgga agacggtgac cgtcttcccg ttaccttgcg cgggccgaag      480
acgccgacgc cgatcaccta ccgcgtgccg atggcctccg cacaggtgaa gtccgccgtg      540
ctgctcgccg gcctcaacac gcccggcatc acgacggtca tcgagccgat catgacgcgc      600
gatcatacgg aaaagatgct gcagggcttt ggcgccaacc ttaccgtcga acggatgcg       660 gacggcgtgc gcaccatccg cctggaaggc cgcggcaagc tcaccggcca agtcatcgac      720
gtgccgggcg acccgtcctc gacggccttc ccgctggttg cggccctgct tgttccgggc      780
tccgacgtca ccatcctcaa cgtgctgatg aaccccaccc gcaccggcct catcctgacg      840
ctgcaggaaa tgggcgccga catcgaagtc atcaacccgc gccttgccgg cggcgaagac      900
gtggcggacc tgcgcgttcg ctcctccacg ctgaagggcg tcacggtgcc ggaagaccgc      960
gcgccttcga tgatcgacga atatccgatt ctcgctgtcg ccgccgcctt cgcggaaggg     1020
gcgaccgtga tgaacggtct ggaagaactc cgcgtcaagg aaagcgaccg cctctcggcc     1080
gtcgccaatg gcctcaagct caatggcgtg gattgcgatg agggcgagac gtcgctcgtc     1140
gtgcgtggcc gccctgacgg caaggggctc ggcaacgcct cgggcgccgc cgtcgccacc     1200
catctcgatc accgcatcgc catgagcttc ctcgtcatgg gctcgtgtc ggaaaaccct      1260 gtcacggtgg acgatgccac gatgatcgcc acgagcttcc cggagttcat ggacctgatg     1320
gccgggctgg gcgcgaagat cgaactctcc gatacgaagg ctgcctga              1368

<210> SEQ ID NO 2
<211> LENGTH: 1278
```

```
<212> TYPE: DNA
<213> ORGANISM: Artificial Sequence
<220> FEATURE:
<223> OTHER INFORMATION: Synthetic polynucleotide

<400> SEQUENCE: 2
ctacccttgt tagtcaaacc acacataaga gaggatggat ttaaaccagt cagcaccgta      60
agtatatagt gaagaaggct gataacacac tctattattg ttagtacgta cgtatttcct    120
tttttgttta gttttgaat ttaattaatt aaaatatata tgctaacaac attaaatttt     180
aaatttacgt ctaattatat attgtgatgt ataataaatt gtcaacctt aaaaattata    240 aaagaaatat taattttgat aaacaacttt tgaaaagtac ccaataatgc tagtataaat    300 agggggcatga ctccccatgc atcacagtgc aatttagctg aagcaaagca atggctactt    360
caaagttgaa aacccagaat gtggttgtat ctctctccct aaccttaacc ttggtactgg    420
tgctactgac cagcaaggca aactcagcgg aaactgttt tttcagctgg aacaagttcg     480
tgccgaagca accaaacatg atcctccaag gagacgctat tgtgacctcc tcgggaaagt    540
tacaactcaa taaggttgac gaaaacggca ccccaaaacc ctcgtctctt ggtcgcgccc    600
tctactccac ccccatccac atttgggaca agaaaccgg tagcgttgcc agcttcgccg    660
cttccttcaa cttcaccttc tatgcccctg acacaaaaag gcttgcagat gggcttgcct    720
tctttctcgc accaattgac actaagccac aaacacatgc aggttatctt ggtcttttca    780
acgaaaacga gtctggtgat caagtcgtcg ctgttgagtt tgacactttc cggaactctt    840
gggatccacc aaatccacac atcggaatta acgtcaattc tatcagatcc atcaaaacga    900
cgtcttggga tttggccaac aataaagtag ccaaggttct cattacctat gatgcctcca    960
ccagcctctt ggttgcttct ttggtctacc cttcacagag aaccagcaat atcctctccg   1020
atgtggtcga tttgaagact tctcttcccg agtgggtgag gatagggttc tctgctgcca   1080
cgggactcga catacctggg gaatcgcatg acgtgctttc ttggtctttt gcttccaatt   1140
tgccacacgc tagcagtaac attgatcctt tggatcttac aagctttgtg ttgcatgagg   1200
ccatctaaat gtgacagatc gaaggaagaa agtgtaataa gacgactctc actactcgat   1260
cgctagtgat tgtcattg                                                 1278

<210> SEQ ID NO 3
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 3
gccctctact ccaccccca                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
gcccatctgc aagccttttt                                                 20

<210> SEQ ID NO 5
<211> LENGTH: 26
<212> TYPE: DNA
```

```
<213> ORGANISM: Artificial Sequence
<220> FEATURE:
<223> OTHER INFORMATION: Synthetic polynucleotide

<400> SEQUENCE: 5
agcttcgccg cttccttcaa cttcac                                       26

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
cctttaggat ttcagcatca gtgg                                         24

<210> SEQ ID NO 7
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 7
gacttgtcgc cgggaat                                                 17

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8
cgcaaccgcc cgcaaatcc                                               19

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9 ctaccctttgt tagtcaaacc acac                                        24

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
caatgacaat cactagcgat cgag                                         24

<210> SEQ ID NO 11
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 11
gaaccttgtg caaattattc aaacc                                        25
```

<210> SEQ ID NO 12
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 12

```
gtccccatag attacataac cgac                                                24
```

<210> SEQ ID NO 13
<211> LENGTH: 6922
<212> TYPE: DNA
<213> ORGANISM: Artificial Sequence
<220> FEATURE:
<223> OTHER INFORMATION: Synthetic polynucleotide

<400> SEQUENCE: 13

```
cctgcatact ttcgttgtgc ttttatattg cctgagtaag tcttttgaaa tgttttaatg        60
aagcagaaaa tgttgattta tggcacacag gggaacaaaa gtctcacttg taatatgata       120
gagcaaaatc tcatttggat taagtagctg ctgtgattct tgtcgtctta ttttcttcct       180
agtgtggtgc aagtaaattg tgcttttggt caatcgcatt tggtatggta cagatcgaag       240
agttttttt ccatgctata caattgagta tgaatatata atgccatctc agcttctgct        300
tgttgctgtc ttgcttaatt gctaaaatca tttgtggtac atacacacac gagtctggca       360
tttttgagt atgatcgtct gcaacagctg ctgtatcttc tcacctagct gctgaaacat        420
taattcttga aacccacact gtttgactca tcagtttcat gcacctgtat gttttttgtt      480
gtacaaatgt ttttcatatg tttaccccaa atattgcaga tgtttgagat tgtgagcctt       540
gccgatgatt tgcttccgca tatccctgcg agaatcatta agttaccaac atattaccat       600
acatataaag gctcttcaac aaagaaatct gcttccatca acaagagggg ggtggttca        660
acaggaaatg aaaggtctgg ccgtgagagg ctattgcgtg agcaacctga gcttttacaa       720
cagtttggta tggatttgtt acccacaatg acacaggtta gtgctggaat tcttttcctg      780
agtcctgaca gccatttcaa ttgctatttg tgttttgtct ttgtgtactt taatagcctg      840
tgtgcttgtt caggtgtatg gttcagtgt aaatgcacca atacgtcaca agtgtttatc       900
tatcattgga aaattaatgt actacagctc cgccgaaaca atccagtctc tccttggcac      960
aacaaacata tccaggtttt ctctctctca cctggaacac acaaaagaga tgcatgtttc     1020
attaatagaa ccgaaaaaat tctcagttca tttctagaga atgatttcag aacaatggat     1080
gttaaaagac aaaaagaaag tctctcaagt ctcaatgtac atacttcttt tccaatccct     1140
tctaagttat ttcatttcca tctgcagctt ccttgcgggc attcttgcat ggaaagatcc     1200
tcaagtgttg attcctgctc ttcagatagc agaaataatg atggaaaagc ttccagagac     1260
attttccatg ttatttgtga gggaaggtgt cgttcatgct gtggagtcac tcatatgttc     1320
agaatcttcc aacaaaatgc cttctcaggt gccacctcag gataaagata agattctgc      1380
catgccatca cgttctagac gtcaacgccg gcgtgcgggt gctgttgcag cagaaaatag     1440
ttcattggat gaatcaaata gttccaacct tggtgttatg tgctcaacag caaccgcttc     1500
agaagctcca acaccagcc ttcgtttcac agttagtgac catgcaaagt cttttcaaaga     1560
taaatacttc ccggcggata ctgattcaag tgatatcggg tttactgatg accttcttaa     1620
actgagggca ctctgtgcaa agttgaatac tgtctctgag aacgtcaaaa caaaagcaaa     1680
```

```
agggaaatca aaagctataa gcactaatt  tttggacatc tcaattgatg ttgaagaaca    1740
attagacaaa ataatatctg aaatgctctc tgagcttagc aaagttaatg gtgtttccac    1800
atttgaattc attagaagtg gtgttgtcat agcgttgctt gactatttgt cctgtgggac    1860
atttgggaag gaaaaggtat ctgaaggaaa cctacctcag cttcgtcagc aggcccttag    1920
acgatacaaa accttcatat ctgttgccct ttctattgat catggacgag atgaaactcc    1980
catggcactg ttggttcaga aactgcaaag tgcattgtct tcgctggaac gtttccctgt    2040
tgtgctcagc cagtctagta ggattggtat tggagggtct cgtctgactt caggtcttag    2100
tgctctggct caaccttca  agcttcgtct ttcccgagct caaggcgaaa aatcacttcg    2160
ggattattca tcaaatattg tgcttatcga cccatttgct agtcttgcat ctgttgaaga    2220
attcctttgg cctagagttc aacgcagtga ggttgcatcg aagcctataa ttccatctgg    2280
taataattct gaatctgggg ttcctggcac cacggctggt gcatcattaa cagctgcaat    2340
ggctcaatct ggtcggcgcc caacaacaag atcaaagtca tctgctgcag gtggtcttac    2400
atctaagaag gattctcatg atgaaagcac tagtactgcc aaaggaaaag gaaaagctat    2460
tgtaaagcca aactcagatg aatcaaaagg acctgactgc tcgcaagcaa attcggaaat    2520
gaaagaaggc taccgaaagt cctcgttcag gtcggtgcag cccacatcga tgtccaagga    2580
gaagtggtgg ctgtggtggg cacacttgcc gatcgggctg ggggcgctca gcggccagag    2640
ggaaccagta ccgggcacgt tgacggtctc gtgcttggcg ttgtagcgga tcaggtaaat    2700
ctcgaggtct tggctgtctt cgatgtagcc gcggagctgg tagcgagtgt aagccttgag    2760
cttggactca tcgatcttct ggtacaagta ggtaggtag  cactcgtcga aagtgcccag    2820
gagagtcacg tagttctcct tgaacacatc gtcgccgccc tggatcgtga tgtcggtgct    2880
gccgcgccag ccgcggtcga gctgctgtt  gatgccgcgg aaattggggt cctggaggag    2940
attcctctcg tcgctgagac gcttggcatg cttcaccttc tcggacagct ccttcttctc    3000
gtcgaggcag aactcatcgg agaggcactc cacgaggttg gagacttggt cgatgtggta    3060
gtcagtgacg tcggtcttca ggccgatctg attgctggac gtgaagagct cattgacagc    3120
cttctgggct ctctccaggt cgtactcggc ttcgaaggtg acctcggctg gcacgaactc    3180
aatgcggtca atgtacacct cattgccgga attgaacacg tgggcgctca gggtgaaaac    3240
gctggagccg ttgagaagt  tgaaggggg  ggtgaaaccc acggtgcgga agctgccgga    3300
ttggaggttg ctgccgctgg acatggtggc ggagaagtta ccctgattga tcggcctgcc    3360
gtcgatggag gtgtggaatt gcaggttggt ggtgctagcg tagcgaatcc tgacgcggta    3420
cctctgggac aggggagcgg tgatgttgac gcggagggtg ctgatctggc ccggggaggt    3480
cctgcgcagg atgtcgccgc ccgtgaagcc tgggcccttc accacggagg tgccgctgcc    3540
caggttggtg gacttggtga gggggatttg ggtgatttgg gaggacggaa tgatattgtt    3600
gaactccgcg ctgcgatgaa tccaggagaa cataggagct ctgatgatgc tcacggacga    3660
gttgctgaag ccggagcgga acatggacac gtggctgagc ctgtgggaaa accctgcct   3720
gggggcaca  ttgttgttct gtggtgggat ctcgtccagg gaatccaccg tgccgctctt    3780
gcggtagaca gcggagggca ggttggagga ggtgccgtag gcgaactcag tgccatccag    3840
gacggacagc tgctggttgt tgataccgat gttgaagggc ctgcggtaca gggtggagct    3900
cagggtgcgg tagacgccct ggcccagctg agcgacgatg cgttgttgtg gagcggcgtt    3960
gcccatcgtg ccgtagagag gaaaggtaaa ctcggggccg ctgaagccga ccggggaggc    4020
catgatctgg tggccggacc agtagtactc gccgcggtgg gcatcggtgt agatagtgat    4080
```

```
gctgttgagg atgtccatca ggtgtgggct cctgatggag ccctcgatgc cctgggcgct      4140 gccccctgaag ctaccgtcga agttctccag gacggggttg gtgtagattt cgcgggtcag     4200
ttgggacacg gtgcggatcg ggtaggtgcg ggagtcgtag ttcgggaaga gggacacaat      4260
gtccaggacg gtgagggtca gctcgcgcct gaactggttg tagcgaatcc agtctctaga      4320
atcagggccc cagacgcgct ccaggccagt gttgtaccag cggacagcgt ggtcggtgta      4380
gttgccgatc agcctggtga ggtcgttgta gcggctgttg atggtggcgg cgtcgaagcc      4440
ccacctctgg ccaaacacgc tgacgtccct cagcacgctg aggtgcaggt tggcggcctg      4500
gacgtacacg gacaggagcg ggacttggta gttctggacg gcgaagagtg ggatggcggt      4560
ggtcagggcg ctgttcatgt cgttgaactg gatgcgcatc tcctcgcgga gagctgggtt      4620 agtgggggtcg gcctcccact cgcggaagct ctcagcgtag atttggtaga ggttgctgag    4680
gccctccagg cggctgatgg cctggttcct ggcgaactcc tcgatcctct ggttgatgag      4740
ctgctcgatt tgcaccagga aggcgtccca ctgggagggg ccaaagatgc cccagatgat     4800
gtccacgagg cccaggacga agccagcgcc tggcacgaac tcgctgagca ggaactgcgt     4860
gagggagagg gagatgtcga tggggggtgta accggtctcg atgcgctcac cgccgagcac    4920
ctcgacctca gggttgctga ggcagttgta cgggatgcac tcgttgatgt ttgggttgtt     4980
gtccatggcc gcttggtatc tgcattacaa tgaaatgagc aaagactatg tgagtaacac     5040
tggtcaacac tagggagaag gcatcgagca agatacgtat gtaaagagaa gcaatatagt     5100
gtcagttggt agatactaga taccatcagg aggtaaggag agcaacaaaa aggaaactct      5160 ttattttttaa attttgttac aacaaacaag cagatcaatg catcaaaata ctgtcagtac    5220
ttatttcttc agacaacaat atttaaaaca agtgcatctg atcttgactt atggtcacaa     5280
taaaggagca gagataaaca tcaaaatttc gtcatttata tttattcctt caggcgttaa     5340
caatttaaca gcacacaaac aaaaacagaa taggaatatc taattttggc aaataataag     5400
ctctgcagac gaacaaatta ttatagtatc gcctataata tgaatcccta tactattgac     5460
ccatgtagta tgaagcctgt gcctaaatta acagcaaact tctgaatcca agtgccctat     5520
aacaccaaca tgtgcttaaa taaataccgc taagcaccaa attacacatt tctcgtattg     5580
ctgtgtaggt tctatcttcg tttcgtacta ccatgtccct atattttgct gctacaaagg     5640
acggcaagta atcagcacag gcagaacacg atttcagagt gtaattctag atccagctaa     5700
accactctca gcaatcacca cacaagagag cattcagaga aacgtggcag taacaaaggc     5760
agagggcgga gtgagcgcgt accgaagacg gtagatctgc tagagtcagc ttgtcagcgt     5820
gtcctctcca aatgaaatga acttccttat atagaggaag ggtcttgcga aggatagtgg     5880
gattgtgcgt catcccttac gtcagtggag atatcacatc aatccacttg ctttgaagac     5940
gtggttggaa cgtcttcttt ttccacgatg ctcctcgtgg gtgggggtcc atctttggga     6000
ccactgtcgg cagaggcatc ttcaacgatg gcctttcctt tatcgcaatg atggcatttg     6060
taggagccac cttcctttc cactatcttc acaataaagt gacagatagc tgggcaatgg      6120
caaaggatgt taaacgttag agtccttcgt ccttcgaagc attatttccc ttgggatata     6180
atgattttcg ggcgaaggtt atgaaggaca taccttcatc agcacaagat ataataatga    6240
agaaggaatc atatgaagta taagagataa cataaacaat tatatattat aatcaactta    6300
tttctatttt attatcatgg aagaatagaa atgatatcaa attacagatg taccttcggc     6360
ttgaaagaag gtaaaagtat aagcgtggcg caaaagcaaa tgccaagtca gcgcgaacag     6420
```

```
tacggaaaca ctgttcatct atttataggc acgagacgca gcccatatga aattacaccc    6480
atgccctcta catttgctaa taactctata gtaatccgtc gaggtctaaa tagccttttc    6540
atctttaagt cggtttcctt ttctgctatt atctcgaagc tcttctgcgc acagcttcgg    6600
ctccgcgaca tccttcgtat tccttttgtg cttcttcaca ctgtggtttt aactcaagtc    6660
cgaagatacc tgttcatgca tcatactcca gaaactttgt taaatcatgt ttttgaggac    6720
cttcagaagc cgaaggccac caacagtagc ccctcgtaat attaatttgt tagaatgata    6780
aatttagatt gcgatatgga cgaaggccct aagccgaagg tccgaaaaaa cacctttcct    6840
ttgctagaat agcaacagtc actgacaagc gggcccttcc agttttcagc gcactaggcg    6900
tataaataag agcgcaccac ga                                             6922
```

<210> SEQ ID NO 14
<211> LENGTH: 1622
<212> TYPE: DNA
<213> ORGANISM: Artificial Sequence
<220> FEATURE:
<223> OTHER INFORMATION: Synthetic polynucleotide

<400> SEQUENCE: 14

```
tcccaatcct ttgacatctg ctccgaagca aagtcagagc gctgcaatgc aaaacggaac      60
gagtgggggc agcagcgcga gcaccgccgc gccggtgtcc ggacccaaag ctgatcatcc     120
atcagctcct gtcaccaaga gagaaatcga tgccagtgcg gtgaagccag agcccgcagg     180
tgatgatgct agaccggtgg aaagcatagg catcgctgaa ccggtggatg ctaaggctga     240
tgcagctccg gctacagatg cggcggcgag tgctccttat gacagggagg ataatgaacc     300 tggcccttg gctgggccta atgtgatgaa cgtcgtcgtg gtggcttctg aatgtgctcc      360
tttctgcaag acaggtaggt tgcatttcag ctgagtttct ccgtccaaaa taagcgactg     420
ctctgacaac cgttgccgca taggtggcct tggagatgtc gtgggtgctt tgcctaaggc     480
tctggcgagg agaggacacc gtgttatggt attcatctct tcattttcg ttatatctat      540 gcaccctacg agagacagca gatactgttt cagctgccat gcgcctgaat gcagattctg     600
aactcttgtc ctttgcgaaa catgggaaaa aaattaagat cacatagtca tacttctgta     660
accacaagtt ttgcctcagt gctctaatgt acttccacaa aaaaaggag gaaattataa      720 ttcatatatg accagaaaag taatgcaatt ttgtgtcctg atgttaggtc gtgataccaa     780
gatatggaga gtatgccgaa gcccgggatt taggtgtaag gagacgttac aaggtagctg     840
gacaggtatg aaaaaagtgg aaacaaagtc gctgtagaac cgatcctgta tgaaagaaag     900
aaaatatgct agacctgatt ttttttcctcc tgtgattttc aggattcaga agttacttat     960
tttcactctt acattgatgg agttgatttt gtattcgtag aagcccctcc cttccggcac    1020
cggcacaata atatttatgg gggagaaaga ttggtaaata ccaattttga agtgcttttg    1080
ctaacagtag aaaatcaagt tggatgcttg tcacatttat ctaaactatg tctctgaatt    1140
taatcacctg atggcaggat attttgaagc gcatgatttt gttctgcaag gccgctgttg    1200
aggtactgct agccattggt ttctaagaaa ttcacaaagt aacaaaaaaa ttatgatggc    1260
ttactggcta ataagaagat aaattcatcg ctggtaaatt ttgataagtc aacagtgacc    1320
aggccccata gaattacaca atatacaccc ttcactgttt agttaatata ttttttcttct   1380 acttttccaa gctgtctatg cacctcattg aatagtttgt tatgacagac tcaattacag    1440
ctcatatggg ctatagttta ttgtgggcg aataaatctg catcatcctc ttttttcaaag    1500 ttattttgaa catttgcagg ttccatggta tgctccatgt ggcggtactg tctatggtga    1560
```

```
tggcaactta gttttcattg ctaatgattg gcataccgca cttctgcctg tctatctaaa    1620
gg                                                                  1622
```

<210> SEQ ID NO 15
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 15

```
ctcccaatcc tttgacatct gc                                              22
```

<210> SEQ ID NO 16
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 16

```
tcgatttctc tcttggtgac agg                                             23
```

<210> SEQ ID NO 17
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 17

```
agcaaagtca gagcgctgca atgca                                           25
```

<210> SEQ ID NO 18
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 18

```
gatgccttct ccctagtgtt ga                                              22
```

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 19

```
ggatgcactc gttgatgttt g                                               21
```

<210> SEQ ID NO 20
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 20

```
agataccaag cggccatgga caacaa                                          26
```

<210> SEQ ID NO 21

```
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 21
ctcccaatcc tttgacatct gc                                           22

<210> SEQ ID NO 22
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 22
gacttgcctg aacactacat cgac                                         24

<210> SEQ ID NO 23
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 23
gacgttctca gagacagtat tcaactttg                                    29

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
actatagggc acgcgtggt                                               19

<210> SEQ ID NO 25
<211> LENGTH: 8605
<212> TYPE: DNA
<213> ORGANISM: Artificial Sequence
<220> FEATURE:
<223> OTHER INFORMATION: Synthetic polynucleotide

<400> SEQUENCE: 25
cctgaattcc agcacactgg cggccgttac tagtggatcc gagctcggta ccaagcttga    60
tgcatagctt gagtattcta cgcgtcacc taaatagctt ggcgtaatca tggtcatagc   120
tgtttcctgt gtgaaattgt tatccgctca caattccaca caacatacga gccggaagca   180
taaagtgtaa agcctggggt gcctaatgag tgagctaact cacattaatt gcgttgcgct   240
cactgcccgc tttccagtcg ggaaacctgt cgtgccagct gcattaatga atcggccaac   300 gcgcgggag aggcggtttg cgtattgggc gctcttccgc ttcctcgctc actgactcgc   360
tgcgctcggt cgttcggctg cggcgagcgg tatcagctca ctcaaaggcg gtaatacggt   420
tatccacaga atcaggggat aacgcaggaa agaacatgtg agcaaaaggc cagcaaaagg   480
ccaggaaccg taaaaaggcc gcgttgctgg cgttttttcca taggctccgc cccccctgacg   540 agcatcacaa aaatcgacgc tcaagtcaga ggtggcgaaa cccgacagga ctataaagat   600
accaggcgtt ccccctgga agctccctcg tgcgctctcc tgttccgacc ctgccgctta   660
ccggatacct gtccgccttt ctcccttcgg gaagcgtggc gctttctcat agctcacgct   720
```

```
gtaggtatct cagttcggtg taggtcgttc gctccaagct gggctgtgtg cacgaacccc    780
ccgttcagcc cgaccgctgc gccttatccg gtaactatcg tcttgagtcc aacccggtaa    840
gacacgactt atcgccactg gcagcagcca ctggtaacag gattagcaga gcgaggtatg    900
taggcggtgc tacagagttc ttgaagtggt ggcctaacta cggctacact agaagaacag    960
tatttggtat ctgcgctctg ctgaagccag ttaccttcgg aaaagagtt ggtagctctt    1020 gatccggcaa acaaaccacc gctggtagcg gtggtttttt tgtttgcaag cagcagatta   1080
cgcgcagaaa aaaggatct caagaagatc ctttgatctt ttctacgggg tctgacgctc    1140
agtggaacga aaactcacgt taagggattt tggtcatgag attatcaaaa aggatcttca    1200
cctagatcct tttaaattaa aaatgaagtt ttagcacgtg tcagtcctgc tcctcggcca    1260
cgaagtgcac gcagttgccg gccgggtcgc gcagggcgaa ctcccgcccc cacgctgct    1320 cgccgatctc ggtcatggcc ggcccggagg cgtcccggaa gttcgtggac acgacctccg   1380
accactcggc gtacagctcg tccaggccgc gcacccacac ccaggccagg gtgttgtccg    1440
gcaccacctg gtcctggacc gcgctgatga acagggtcac gtcgtcccgg accacaccgg    1500
cgaagtcgtc ctccacgaag tcccgggaga acccgagccg gtcggtccag aactcgaccg    1560
ctccggcgac gtcgcgcgcg gtgagcaccg gaacggcact ggtcaacttg gccatggtgg    1620
ccctcctcac gtgctattat tgaagcattt atcagggtta ttgtctcatg agcggataca    1680
tatttgaatg tatttagaaa aataaacaaa taggggttcc gcgcacattt ccccgaaaag    1740
tgccacctga tgcggtgtga ataccgcac agatgcgtaa ggagaaaata ccgcatcagg    1800
aaattgtaag cgttaataat tcagaagaac tcgtcaagaa ggcgatagaa ggcgatgcgc    1860
tgcgaatcgg gagcggcgat accgtaaagc acgaggaagc ggtcagccca ttcgccgcca    1920
agctcttcag caatatcacg ggtagccaac gctatgtcct gatagcggtc cgccacaccc    1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg    2100
gcgaacagtt cggctggcgc gagccccctga tgctcttcgt ccagatcatc ctgatcgaca    2160
agaccggctt ccatccgagt acgtgctcgc tcgatgcgat gtttcgcttg gtggtcgaat    2220
gggcaggtag ccggatcaag cgtatgcagc cgccgcattg catcagccat gatggatact    2280
ttctcggcag gagcaaggtg agatgacagg agatcctgcc ccggcacttc gcccaatagc    2340
agccagtccc ttcccgcttc agtgacaacg tcgagcacag ctgcgcaagg aacgcccgtc    2400
gtggccagcc acgatagccg cgctgcctcg tcttgcagtt cattcagggc accggacagg    2460
tcggtcttga caaaaagaac cgggcgcccc tgcgctgaca gccggaacac ggcggcatca    2520
gagcagccga ttgtctgttg tgcccagtca tagccgaata gcctctccac ccaagcggcc    2580
ggagaacctg cgtgcaatcc atcttgttca atcatgcgaa acgatcctca tcctgtctct    2640
tgatcagagc ttgatcccct gcgccatcag atccttggcg gcaagaaagc catccagttt    2700
actttgcagg gcttcccaac cttaccagag ggcgccccag ctggcaattc cggttcgctt    2760
gctgtccata aaaccgccca gtctagctat cgccatgtaa gcccactgca agctacctgc    2820
tttctctttg cgcttgcgtt ttcccttgtc cagatagccc agtagctgac attcatccgg    2880
ggtcagcacc gtttctgcgg actggctttc tacgtgaaaa ggatctaggt gaagatcctt    2940
tttgataatc tcatgcctga catttatatt cccagaacat caggttaat ggcgttttg    3000 atgtcatttt cgcggtggct gagatcagcc acttcttccc cgataacgga gaccggcaca    3060
```

```
ctggccatat cggtggtcat catgcgccag ctttcatccc cgatatgcac caccgggtaa    3120
agttcacggg agactttatc tgacagcaga cgtgcactgg ccaggggat caccatccgt     3180
cgccccggcg tgtcaataat atcactctgt acatccacaa acagacgata acggctctct    3240
cttttatagg tgtaaacctt aaactgccgt acgtataggc tgcgcaactg ttgggaaggg    3300
cgatcggtgc gggcctcttc gctattacgc cagctggcga aaggggatg tgctgcaagg     3360
cgattaagtt gggtaacgcc agggttttcc cagtcacgac gttgtaaaac gacgccagt     3420
gaattgtaat acgactcact atagggcgaa ttgggccctc tagactaccc ttgttagtca    3480
aaccacacat aagagaggat ggatttaaac cagtcagcac cgtaagtata tagtgaagaa    3540
ggctgataac acactctatt attgttagta cgtacgtatt tccttttttg tttagttttt    3600
gaatttaatt aattaaaata tatatgctaa caacattaaa ttttaaattt acgtctaatt    3660
atatattgtg atgtataata aattgtcaac ctttaaaaat tataaaagaa atattaattt    3720
tgataaacaa cttttgaaaa gtacccaata atgctagtat aaatagggc atgactcccc     3780
atgcatcaca gtgcaattta gctgaagcaa agcaatggct acttcaaagt tgaaaaccca    3840
gaatgtggtt gtatctctct ccctaacctt aaccttggta ctggtgctac tgaccagcaa    3900
ggcaaactca gcgaaactg tttctttcag ctggaacaag ttcgtgccga agcaaccaaa     3960
catgatcctc caaggagacg ctattgtgac ctcctcggga aagttacaac tcaataaggt    4020
tgacgaaaac ggcaccccaa aaccctcgtc tcttggtcgc gccctctact ccaccccat    4080
ccacatttgg gacaaagaaa ccggtagcgt tgccagcttc gccgcttcct tcaacttcac    4140
cttctatgcc cctgacacaa aaaggcttgc agatgggctt gccttctttc tcgcaccaat    4200
tgacactaag ccacaaacac atgcaggtta tcttggtctt ttcaacgaaa acgagtctgg    4260
tgatcaagtc gtcgctgttg agtttgcac tttccggaac tcttgggatc caccaaatcc     4320
acacatcgga attaacgtca attctatcag atccatcaaa acgacgtctt gggatttggc    4380
caacaataaa gtagccaagg ttctcattac ctatgatgcc tccaccagcc tcttggttgc    4440
ttctttggtc taccccttcac agagaaccag caatatcctc tccgatgtgg tcgatttgaa    4500
gacttctctt cccgagtggg tgaggatagg gttctctgct gccacgggac tcgacatacc    4560
tggggaatcg catgacgtgc tttcttggtc ttttgcttcc aatttgccac acgctagcag    4620
taacattgat cctttggatc ttacaagctt tgtgttgcat gaggccatct aaatgtgaca    4680
gatcgaagga agaaagtgta ataagacgac tctcactact cgatcgctag tgattgtcat    4740
tggcggccgc cagtgtgatg gatatctgca gaattcaggg aaccttgtgc aaattattca    4800
aaccctttcaa tttaaccgat gctaatgagt tattttttgca tgctttaatt tgtttctatc   4860
aaatgtttat tttttttttac tagaaataac ttattgcatt tcattcaaaa taagatcata    4920
catacaggtt aaaataaaca tagggaaccc aaatggaaaa ggaaggtggc tcctacaaat    4980
gccatcattg cgataaagga aaggccatcg ttgaagatgc ctctgccgac agtggtccca    5040
aagatggacc cccacccacg aggagcatcg tggaaaaaga agacgttcca accacgtctt    5100
caaagcaagt ggattgatgt gatatctcca ctgacgtaag ggatgacgca caatcccact    5160
atccttcgca agacccttcc tctatataag gaagttcatt tcatttggag aggacacgct    5220
gacaagctga ctctagcaga tctttcaaga atggcacaaa ttaacaacat ggcacaaggg    5280
atacaaaccc ttaatcccaa ttccaatttc cataaaccc aagttcctaa atcttcaagt     5340
tttcttgttt ttggatctaa aaaactgaaa aattcagcaa attctatgtt ggttttgaaa    5400
aaagattcaa tttttatgca aaagttttgt tcctttagga tttcagcatc agtggctaca    5460
```

```
gcctgcatgc ttcacggtgc aagcagccgg cccgcaaccg cccgcaaatc ctctggcctt      5520
tccggaaccg tccgcattcc cggcgacaag tcgatctccc accggtcctt catgttcggc      5580
ggtctcgcga gcggtgaaac gcgcatcacc ggccttctgg aaggcgagga cgtcatcaat      5640
acgggcaagg ccatgcaggc catgggcgcc aggatccgta aggaaggcga cacctggatc      5700
atcgatggcg tcggcaatgg cggcctcctg gcgcctgagg cgccgctcga tttcggcaat      5760
gccgccacgg gctgccgcct gaccatgggc ctcgtcgggg tctacgattt cgacagcacc      5820
ttcatcggcg acgcctcgct cacaaagcgc ccgatgggcc gcgtgttgaa cccgctgcgc      5880
gaaatgggcg tgcaggtgaa atcggaagac ggtgaccgtc ttcccgttac cttgcgcggg      5940
ccgaagacgc cgacgccgat cacctaccgc gtgccgatgg cctccgcaca ggtgaagtcc      6000
gccgtgctgc tcgccggcct caacacgccc ggcatcacga cggtcatcga gccgatcatg      6060
acgcgcgatc atacggaaaa gatgctgcag ggctttggcg ccaaccttac cgtcgagacg      6120
gatgcggacg gcgtgcgcac catccgcctg aaggccgcg gcaagctcac cggccaagtc      6180
atcgacgtgc cgggcgaccc gtcctcgacg gccttcccgc tggttgcggc cctgcttgtt      6240
ccgggctccg acgtcaccat cctcaacgtg ctgatgaacc ccaccgcac cggcctcatc      6300 ctgacgctgc aggaaatggg cgccgacatc gaagtcatca cccgcgcct tgccggcggc      6360 gaagacgtgg cggacctgcg cgttcgctcc tccacgctga agggcgtcac ggtgccggaa      6420
gaccgcgcgc cttcgatgat cgacgaatat ccgattctcg ctgtcgccgc cgccttcgcg      6480
gaaggggcga ccgtgatgaa cggtctggaa gaactccgcg tcaaggaaag cgaccgcctc      6540
tcggccgtcg ccaatggcct caagctcaat ggcgtggatt gcgatgaggg cgagacgtcg      6600
ctcgtcgtgc gtggccgccc tgacggcaag gggctcggca acgcctcggg cgccgccgtc      6660
gccacccatc tcgatcaccg catcgccatg agcttcctcg tcatgggcct cgtgtcggaa      6720
aaccctgtca cggtggacga tgccacgatg atcgccacga gcttcccgga gttcatggac      6780
ctgatggccg ggctgggcgc gaagatcgaa ctctccgata cgaaggctgc ctgatgagct      6840
cgaattcgag ctcggtaccg gatccaattc ccgatcgttc aaacatttgg caataaagtt      6900
tcttaagatt gaatcctgtt gccggtcttg cgatgattat catataattt ctgttgaatt      6960
acgttaagca tgtaataatt aacatgtaat gcatgacgtt atttatgaga tgggttttta      7020
tgattagagt cccgcaatta tacatttaat acgcgataga aaacaaaata tagcgcgcaa      7080
actaggataa attatcgcgc gcggtgtcat ctatgttact agatcgggga tcgatccccc      7140
accggtcctt catgttcggc ggtctcgcga gcggtgaaac gcgcatcacc ggccttctgg      7200
aaggcgagga cgtcatcaat acgggcaagg ccatgcaggc catgggcgcc aggatccgta      7260
aggaaggcga cacctggatc atcgatggcg tcggcaatgg cggcctcctg gcgcctgagg      7320
cgccgctcga tttcggcaat gccgccacgg gctgccgcct gaccatgggc ctcgtcgggg      7380
tctacgattt caagcgcatc atgctgggaa attttagcga gattataagt atcttcctgg      7440
ggatctctgc tgttactggt gaatagtgag acagagtctt ctgagctcat aggataaaat      7500
aaattataat tagtaaattt tttaattaaa taaatcaatt acttcataaa taatttttt      7560 tatagaatat gttgacattc tagctggata tagaactaat ataagaaac cttaaaaatt      7620 ttgtttggaa gaatatgtta ttgaaagaca aatctaatta agtttatcag ggtcatttgt      7680
tgaagatagg aaaccttcag caatttgaat attaagtaac tgcttctccc agaatgatcg      7740
gagtttctcc tcctgctatt acatgaaaaa aaataaaaaa taaaaaaaag ataagattaa      7800
```

```
gcttcaacat gtgaaggagt agtacactca ccagtgaccc taataggcaa cagcatgaaa    7860
aaaaataaaa aagaataaaa atagcatcta catatagctt ctcgttgtta gaaaaacaaa    7920
actatttggg atcggagaag aactgtttga ggcgaatggc ctggtcgtcg cggccatcgt    7980
cgagaagttc gtgaagaagc tcgaatgcgg tgagaaggta gttctcttcc aacagaaagt    8040
tcaccacgca attgcacagc gaagatctct ccacgtccat tttctctctc tgtctctgat    8100
cttaagccat tcattcaaga caagacaaga gaagagaaga gaagagaaga gaacactctc    8160
agtcagatcg tggtttcaac tttcaagact gtgctagcta gttaggttaa attgaacgaa    8220
gacctcgccg tcagacagag tcttctgtga ggtactcttc tttctcttca ccgttccaat    8280
ttgtgttttc tatttggcgc ctccttgtac ttctgccaac tatatataat aggaatggat    8340
atatgaattg ttcgtatgcc agtgaatttt gccataacct ttagaattta aaacgaggat    8400
atgctttgtt gatcacaaga ttaagaaatt ctgagggaga ttacaatacg aaattaagcc    8460
tttctctagt acttggactc caatttaata cttagggttg tttatgagtt atgacattta    8520
ggtgtggatt aatgttattt atatcgactg tattggcttc ctagatatgg gcattgtttt    8580
tgtcggttat gtaatctatg gggac                                         8605
```

STANDARD PLASMID FOR ASSAYING GENETICALLY MODIFIED ORGANISM, AND ANALYSIS METHOD AND ASSAY KIT USING SAME

The present application is a Continuation-in-part Application of International Application No. PCT/KR2014/004402 filed May 16, 2014, which claims priority from Korean Patent Application No. 10-2013-0056073 filed on May 16, 2013, of which contents are incorporated by reference herein in their entirety.

TECHNICAL FIELD

The present invention relates to a standard plasmid for assaying a transgene in a genetically modified organism, a method for quantitatively analyzing a target transgene within the genetically modified organism using the standard plasmid, and a kit for assaying the genetically modified organism including the standard plasmid.

BACKGROUND ART

Genetically modified food are food products derived from genetically modified organism and obtained from the latest technology for improving shelf life, nutritional content, color, flavor, and texture of food. The GMO refers to organisms in which productivity is increased by artificially separating and combining useful genes of animals and plants or microorganisms unlike developing by the existing crop breeding, that is, organisms having a new genetic trait obtained by inserting external derived gene into genetic material of reference organisms using modern biotechnology rather than traditional breeding or natural recombination. In addition, genetic recombination food refers to food produced by using the genetically modified organism as raw materials. In general, in order to increase productivity of genetically modified agricultural products, genes related with herbicide-resistance, insect resistance, disease resistance, cold resistance, and the like, have been introduced into the agricultural products. These days, many GMO foods are distributed, and among them, soybean foods are largely occupied. In addition to soybean, other various GMO foods including corn, papaya, pumpkin, and the like, are also distributed. Meanwhile, according to current controversies related to human health by the GMO, there is growing concern of consumers and farmers in respect to the GMO all over the world. Accordingly, in order to commercialize genetically modified crop, evaluation of environmental hazards, human health and food safety is required, and in relevant countries to import the genetically modified agricultural products, a regulatory system including GMO mandatory labeling has been established. In Korea, a label, of which food that has 3% or more of genetically modified plants introduced, needs to be marked as a genetically modified plant has been enforced. Other countries face a similar situation even though there is a difference in an incorporation tolerance. Accordingly, accurate analysis techniques for quantitatively measuring an incorporation ratio are required, in addition to qualitative analysis for measuring whether the GMO is incorporated.

The quantitative analysis of the GMO is largely divided into a protein analysis and a DNA analysis. In general, ELISA method targeting a protein which is expressed from a foreign gene introduced into the genetically modified plants has drawbacks that a detection intensity is lower than the PCR method, and a heat treatment may cause a denaturation of the protein. A technology of quantifying a foreign gene introduced into the genetically modified plant using a real-time PCR is widely employed. The real-time PCR renders a simultaneous amplication of the foreign gene and a quantitative monitoring the amount of amplification product. Quantitative analysis data may be obtained as a ratio of the foreign gene and endogenous genes with regard to predetermined amounts of a standard material by employing a real-time PCR, in which a fluorescent probe or certified reference material (CRM) or a standard plasmid is used as a standard material, in addition to a primer set required for the qualitative PCR.

Above all things, for accurate and precise analysis of the incorporation tolerance of the genetically modified plant, the standard material used for analysis is significantly important. Currently, GMO soy is neither cultivated and produced nor distributed in Korea. However, according to a government announcement, 932,000 tons of GMO soybeans (edible) corresponding to 77% of the total bean import volume, were imported in 2008. The GMO soy is used as a raw food material by extracting oils and protein. Soy protein is mainly used for bread, snack, processed meat products, baby food, and nutritional supplements, soybean fiber is used for wheat bread, cereals, snack processed goods, and soybean oil is used for salad oil, salad dressings, shortenings and raw materials of processed food, and the like. A GMO labeling requirement of soybeans and and a strict enforcement thereof are a sound public policy. Thus, there is a need for an improved standard material which can be used to accurately detecting and quantifying a foreign gene in a GMO. In addition, for a quantitative analysis of corns including various corn varieties, the use of one single standard material does not produce an accurate result because corns have different expression amounts depending on the variety. Also, a protein detection method has a limitation in detecting proteins expressed from a foreign gene in processed foods or raw materials containing GMOs, because recombinant proteins undergo denaturation or lysis during the food processing steps. That is, the standard material for analyzing genetically modified corns is required to have a long shelf-life as well as stability and homogeneity of the standard material itself, and such a standard material is needed.

DISCLOSURE

Technical Problem

The present invention is provided to solve problems of the related art.

An object of the present invention is to provide a standard plasmid for assaying a genetically modified organism, particularly, a genetically modified organism containing a 5-enoyl-4-pyruvylshikimate-3-phosphate synthase (EPSPS) gene.

Another object of the present invention is to provide a method for quantitatively analyzing the genetically modified organism using the standard plasmid, particularly, a method for quantitatively analyzing a target transgene within the genetically modified organism containing the EPSPS gene.

Still another object of the present invention is to provide a kit for assaying the genetically modified organism including the standard plasmid, particularly, a kit for assaying the genetically modified organism including the EPSPS gene.

Still another object of the present invention is to provide a kit for assaying the genetically modified organism including protein expressed from the standard plasmid, particularly, a kit for assaying the genetically modified organism including the EPSPS gene.

Still another object of the present invention is to provide a standard plasmid for assaying a genetically modified organism, particularly, a genetically modified organism containing a cry1Ab gene.

Still another object of the present invention is to provide a method for quantitatively analyzing the genetically modified organism using the standard plasmid, particularly, a method for quantitatively analyzing a target transgene within the genetically modified organism containing the cry1Ab gene.

Still another object of the present invention is to provide a kit for assaying the genetically modified organism including the standard plasmid, particularly, a kit for assaying the genetically modified organism including the cry1Ab gene.

Still another object of the present invention is to provide a kit for assaying the genetically modified organism including protein expressed from the standard plasmid, particularly, a kit for assaying the genetically modified organism including the cry1Ab gene.

Technical Solution

In one general aspect, there is provided a standard plasmid for assaying a genetically modified organism, the standard plasmid including: a Lectin gene and a 5-enoyl-4-pyruvyl-shikimate-3-phosphate synthase (EPSPS) gene.

According to an exemplary embodiment of the present invention, the EPSPS gene may include 5' flanking sequence and 3' flanking sequence.

The EPSPS gene included in the standard plasmid may include base sequence of SEQ ID NO: 1, and the Lectin gene included in the standard plasmid may include base sequence of SEQ ID NO: 2.

The standard plasmid for assaying the genetically modified organism may include a sequence of the EPSPS gene that is a GM gene provided by Food and Drug Administration and IRMM and a sequence of the Lectin gene that is an endogene.

Preferably, the EPSPS gene included in the standard plasmid may include the 5' flanking sequence and the 3' flanking sequence. The standard plasmid may have advantage in that varieties that are analysis targets are capable of being classified by including the 5' flanking sequence and the 3' flanking sequence of the EPSPS gene. The varieties may not be classified only with the GM gene; however, by including the flanking sequences, the varieties may be determined whether or not they are the same as GTS 40-3-2 (hereinafter, referred to as Roundup Ready Soya (RRS) in the present specification and claims), by qualitative PCR.

According to an exemplary embodiment of the present invention, the standard plasmid having the constitution of FIG. 1 was prepared so that regions including the 5' flanking sequence and the 3' flanking sequence of the EPSPS gene have base sequence of SEQ ID NO: 25, and as a result, it was confirmed that determination accuracy and sensitivity of the RRS variety were increased as compared to the existing method. The results may not be obtained at the time of including the gene only without including the existing flanking sequence.

In particular, whether or not the GM gene is incorporated and RRS variety may be simultaneously determined by amplifying the EPSPS gene and the regions including the 5' flanking sequence and the 3' flanking sequence of the EPSPS gene using 35Sbean3F of SEQ ID NO: 11 and GW1R of SEQ ID NO: 12 (FIG. 17b). The result of FIG. 17b is remarkably improved as compared to the result of the existing GM qualitative analysis (FIG. 17a) including determining whether or not GM gene is incorporated by primary screening of gene regulatory regions and endogenes for expression of transgenes and performing qualitative PCR using a gene-specific primer to determine GM varieties.

In addition, an event of the genetically modified plant may be determined by using the standard plasmid of the present invention. Accordingly, the standard plasmid of the present invention is more appropriately used as a standard material for detecting GMO since a number of events of the genetically modified organism as well as varieties of the genetically modified organism are capable of being assayed.

More preferably, the standard plasmid may be pBlunt-9kbLE having a genetic map as shown in FIG. 1. In an exemplary embodiment of the present invention, the pBlunt-9kbLE plasmid is obtained by producing PCR products of the Lectin gene amplified by a forward primer leK1F (SEQ ID NO: 9) and a reverse primer leK1R (SEQ ID NO: 10) for securing a Lectin insertion gene and PCR products of the EPSPS gene amplified by a forward primer 35Sbean3F (SEQ ID NO: 11) and a reverse primer GW1R (SEQ ID NO: 12) for securing an RRS insertion gene, respectively, treating each PCR product with restriction enzymes, and inserting each treated product into a pCR-Blunt vector. The pBlunt-9kbLE plasmid may be used as the standard plasmid for a quantitative assay method in which the gene incorporation ratio of the genetically modified organism according to the present invention is calculated.

The genetically modified plant which is an assay target of the standard plasmid according to the present invention may be a soybean RRS, but the present invention is not limited thereto.

The "soybean RRS" of the present invention is a herbicide-tolerant soybean developed by using recombinant DNA technology from Monsanto Korea Co., Ltd., and means a soybean into which the EPSPS gene which is a gene expressing EPSPS protein of CP4 bacteria which is not affected by herbicide, glyphosate, is introduced. The glyphosate is specifically bound to 5-enoyl-4-pyruvylshikimate-3-phosphate synthase (hereinafter, referred to as 'EPSPS protein') which is one enzyme of a synthesis pathway (shikimate pathway) of specific aromatic amino acid of plants or microorganisms to thereby inhibit activity thereof, and accordingly, when this pesticide is sprayed, essential amino acids are not synthesized, such that almost all plants are killed. However, the plant into which the EPSPS gene is introduced, has an insensitive target site which is not affected by glyphosate, such that a herbicide-tolerant soybean into which a gene expressing CP4 EPSPS protein is introduced may not be killed but may grow even if the glyphosate is sprayed. As described above, the soybean RRS contains the EPSPS gene, such that the soybean RRS is appropriate as the genetically modified organism for quantitative analysis using the standard plasmid of the present invention. Meanwhile, the present invention is not necessarily limited thereto, and it is obvious that any genetically modified organism containing the EPSPS gene may be an assay target according to the present invention.

In another general aspect, there is provided a method for quantitatively analyzing a target transgene within a genetically modified organism using the standard plasmids as described above.

In an exemplary embodiment of the present invention, the quantitative analysis method includes:

i) preparing a series of dilutions of the standard plasmid of claim 1;

ii) performing a real-time PCR on the dilutions of the standard plasmid and a DNA sample of the genetically modified plant, respectively, using a PCR primer set and a probe which bind to the target transgene and the standard plasmid;

iii) providing a standard quantitative curve from measured amounts of PCR products obtained in step ii) by using the dilutions of the standard plasmid; and iv) determining an incorporation ratio of the target transgene by comparing the measured amounts of PCR products obtained from the DNA of the generically modified plant, with the standard quantitative curve provided in step iii).

The genetically modified organism in the quantitative analysis method is preferably soybean RRS, but the present invention is not limited thereto.

When the real-time PCR is performed, the amounts of endogenes and transgenes may be calculated by measuring an amount of fluorescence expressed in the PCR amplification using bi-directional primers and probe for detection specifically bound to DNA of the endogenes and the transgenes. That is, the quantitative analysis method is a method for analyzing what percentage of the genetically modified plant is contained by calculating a relative ratio of the transgenes to the endogenes that are necessarily contained in the corresponding plant.

According to an exemplary embodiment of the present invention, the incorporation ratio in the sample of the genetically modified plant may be analyzed by performing real-time PCR on the standard material using a probe for detection and a primer for detecting the transgenes and a primer for detecting the endogenes to measure fluorescence, thereby calculating a standard curve showing PCR cycle number with respect to the gene copy number, and then comparing the obtained results with the real-time PCR product obtained from the analysis sample.

Preferably, the PCR primer sets of step ii) in the quantitative analysis method may be a primer set of SEQ ID NOS: 3 and 4 and a primer set of SEQ ID NOS: 6 and 7, and the probe may consist of SEQ ID NOS: 5 and 8, but the present invention is not limited thereto. Further, the probe means a probe for detection in which a fluorescent material is introduced into base sequence for quantitative analysis at the time of performing real-time PCR. Kinds of the probes for detection may be appropriately selected according to kinds of endogens and transgenes by a person skilled in the art.

The standard quantitative curve in step iii) of the quantitative analysis method may be calculated by performing real-time PCR on a plurality of standard samples each having a different gene copy number by diluting the standard plasmid DNAs at each predetermined ratio, and applying the PCR cycle number to the gene copy number obtained therefrom. Specifically, when the plurality of samples are prepared to have copy numbers with predetermined intervals by appropriately diluting DNA of the standard material in which the incorporation ratio is known or to have a predetermined incorporation ratio by mixing a genetically modified plant DNA with a genetically non-modified plant DNA at a predetermined ratio, and are then subjected to real-time PCR, degree of fluorescence according to PCR cycle number may be measured. Here, a portion in which fluorescence signal of a standard solution is exponentially amplified is determined as a Threshold line (Th. Line), and a cycle number of a point at which the determined threshold line (Th. Line) and the amplification curve of the standard solution cross each other, refers to a threshold cycle (Ct), wherein the Ct indicates the time point representing the most reproducible correlation with the initial concentration (gene copy number) of the sample, which is the most important value in quantitative analysis using real-time PCR. In the real-time PCR, the standard curve includes a value obtained by converting the gene copy number of the standard material at Ct value into a log value on X axis and the PCR cycle number to the gene copy number on Y axis. Then, the gene copy number of the analysis sample may be appreciated by applying the fluorescence amount of the analysis sample to the standard curve.

In still another general aspect, there is provided a kit for assaying a genetically modified plant including the standard plasmid as described above.

The genetically modified plant which is the target of the kit for the assay is preferably the genetically modified soybean of RRS variety, but the present invention is not limited thereto.

Preferably, the kit for the assay may include primer sets of SEQ ID NOS: 3 and 4, and 6 and 7, and a probe of SEQ ID NOS: 5 and 8. The present invention provides the kit for assaying the genetically modified plant including the standard plasmid, thereby making it possible to perform quantitative analysis using real-time PCR for assaying the genetically modified plant containing the EPSPS gene.

The kit may additionally include reagents for transcription, amplification, and for detecting products, and instructions therefor. For example, the kit may contain transcriptase, deoxynucleotide, thermostable polymerase which is appropriate for DNA amplification reaction and reagents for labeling and detecting nucleic acid.

In still another general aspect, there is provided a kit for assaying a genetically modified organism including protein expressed from the standard plasmid as described above. The standard plasmid of the present invention may include a T7 promoter, and the EPSPS gene which is a transgene introduced into the standard plasmid and the Lectin gene which is an endogene are operably linked to the T7 promoter. Therefore, EPSPS protein and Lectin protein may be expressed from the standard plasmid of the present invention in a suitable environment for expressing the proteins. The expressed proteins may be used as the standard protein for quantitative analysis or qualitative analysis by an enzyme linked immunosorbent assay (ELISA).

In still another general aspect, there is provided a standard plasmid for assaying a genetically modified organism including: a ssIIb gene and a cry1Ab gene.

According to an exemplary embodiment of the present invention, the present invention provides the standard plasmid for assaying the genetically modified organism, wherein the cry1Ab gene includes 5' flanking sequence and 3' flanking sequence.

The cry1Ab gene included in the standard plasmid may include base sequence of SEQ ID NO: 13, and the ssIIb gene included in the standard plasmid may include base sequence of SEQ ID NO: 14, but the present invention is not limited thereto.

The standard plasmid for assaying the genetically modified organism of the present invention may include a sequence of GM maize MON810 (cry1Ab gene sequence) and a sequence of an endogene (ssIIb, Starch Synthase IIb) provided by Food and Drug Administration and IRMM. The currently commercially available existing standard plasmid ERM-AD413 for analyzing GM maize MON810 includes a hmg (high mobility group) gene, which has a gene constitution that is not appropriate for national test methods, instead of including the ssIIb gene clearly defined in the Food and Drug Administration Standards codex. Meanwhile, the standard plasmid of the present invention includes the endogene ssIIb gene which is clearly defined in the Food and Drug Administration Standards codex.

Preferably, the cry1Ab gene included in the standard plasmid may include the 5' flanking sequence and the 3' flanking sequence. The standard plasmid may have advantage in that varieties that are analysis targets are capable of being classified by including the 5' flanking sequence and the 3' flanking sequence of the cry1Ab gene. The varieties may not be classified only with the GM gene (for example, the cry1Ab gene is a GM gene of GM maize Bt11 as well as GM maize MON810); however, by including the flanking sequences, the varieties may be determined whether or not they are the same as GM maize MON810 by qualitative PCR.

In addition, an event of the genetically modified plant may be determined by using the standard plasmid of the present invention. Accordingly, the standard plasmid of the present invention is more appropriately used as a standard material for detecting GMO since events of the genetically modified organism as well as varieties of the genetically modified organism are capable of being classified.

More preferably, the standard plasmid may be pBlunt-12kbMS having a genetic map as shown in FIG. 9. In an exemplary embodiment of the present invention, the pBlunt-12kbMS plasmid is obtained by producing PCR products of the ssIIb genes amplified by a forward primer SSIIb 1-5 (SEQ ID NO: 21) and a reverse primer SSIIb 2-3 (SEQ ID NO: 22) for securing a ssIIb insertion gene and PCR products of the cry1Ab genes amplified by a forward primer GWMcry3F-1 (SEQ ID NO: 23) and a reverse primer AP2 (SEQ ID NO: 24) for securing a GM maize MON810 insertion gene, respectively, treating each PCR product with restriction enzymes, and inserting each treated product into a pCR-Blunt vector. The pBlunt-12kbMS plasmid may be used as the standard plasmid for a quantitative assay method in which the gene incorporation ratio of the genetically modified organism according to the present invention is calculated.

The genetically modified plant which is the target for assaying the standard plasmid according to the present invention is preferably GM maize MON810, but the present invention is not limited thereto.

"GM maize MON810" of the present invention means a genetically modified corn into which the cry1Ab gene is introduced, the cry1Ab gene producing Cry1Ab protein which is a Bt protein showing toxicity in a pest derived from *Bacillus thuringiensis* Bt. Delta-endotoxins such as Cry1Ab protein are positioned at a midgut epithelium of the insect (brush border) and are selectively bound to specific sites to be acted. After being bound, cation spores paralyze the insect by impeding flow of midgut ions, and eventually, lead to death of the insect. The cry1Ab serves as a pesticide only for a lepidopteran insect, and an activity thereof is directly caused from the presence of the binding site in the target insect. Since the binding site does not exist on the surface of a human intestinal cell, these proteins do not act on animals or human. As described above, the GM maize MON810 contains the cry1Ab gene, such that the GM maize MON810 is appropriate as the genetically modified organism for quantitative analysis according to the present invention. Meanwhile, the present invention is not necessarily limited thereto, and it is obvious that any genetically modified organism containing the cry1Ab gene may be an assay target according to the present invention.

In another general aspect, there is provided a method for quantitatively analyzing a target transgene within a genetically modified organism using the standard plasmid as described above.

The quantitative analysis method may include:
i) preparing a series of dilutions of the standard plasmid of claim 1;
ii) performing a real-time PCR on the dilutions of the standard plasmid and a DNA sample of the genetically modified plant, respectively, using a PCR primer set and a probe which bind to the target transgene and the standard plasmid;
iii) providing a standard quantitative curve from measured amounts of PCR products obtained in step ii) by using the dilutions of the standard plasmid; and
iv) determining an incorporation ratio of the target transgene by comparing the measured amounts of PCR products obtained from the DNA of the generically modified plant, with the standard quantitative curve provided in step iii).

The genetically modified organism in the quantitative analysis method is preferably GM maize MON810, but the present invention is not limited thereto.

When the real-time PCR is performed, the amounts of endogenes and transgenes may be calculated by measuring an amount of fluorescence expressed in the PCR amplification using bi-directional primers and probe for detection specifically bound to DNA of the endogenes and the transgenes. That is, the quantitative analysis method is a method for analyzing what percentage of the genetically modified plant is contained by calculating a relative ratio of the transgenes to the endogens that is necessarily contained in the corresponding plant.

According to an exemplary embodiment of the present invention, the incorporation ratio in the sample of the genetically modified plant may be analyzed by performing real-time PCR on the standard material using a probe for detection and a primer for detecting the transgene and a primer for detecting the endogene to measure fluorescence, thereby calculating a standard curve showing PCR cycle number with respect to the gene copy number, and then comparing the obtained results with the real-time PCR product obtained from the analysis sample.

Preferably, the PCR primer sets of step ii) in the quantitative analysis method may be a primer set of SEQ ID NOS: 15 and 16 and a primer set of SEQ ID NOS: 18 and 19, and the probe may consist of SEQ ID NOS: 17 and 20, but the present invention is not limited thereto. Further, the probe means a probe for detection in which a fluorescent material is introduced into base sequence for quantitative analysis at the time of performing real-time PCR. Kinds of the probe for detection may be appropriately selected according to kinds of endogens and transgenes by a person skilled in the art.

The standard quantitative curve in step iii) of the quantitative analysis method may be calculated by performing real-time PCR on a plurality of standard samples each having different gene copy number by diluting the standard plasmid DNAs at each predetermined ratio, and applying the PCR cycle number to the gene copy number obtained therefrom. Specifically, when the plurality of samples are prepared to have copy numbers with predetermined intervals by appropriately diluting DNA of the standard material in which the incorporation ratio is known or to have a predetermined incorporation ratio by mixing a genetically modified plant DNA and a genetically non-modified plant DNA at a predetermined ratio, and are then subjected to real-time PCR, degree of fluorescence according to PCR cycle number may be measured. Here, a portion in which fluorescence signal of a standard solution is exponentially amplified is determined as a Threshold line (Th. Line), and a cycle number of a point at which the determined threshold line (Th. Line) and the amplification curve of the standard solution cross each other, refers to a threshold cycle (Ct), wherein the Ct indicates the time point representing the most reproducible correlation with the initial concentration (gene copy number) of the sample, which is the most important value in quantitative analysis using real-time PCR. In the real-time PCR, the standard curve includes a value obtained by converting the gene copy number of the standard material at Ct value into a log value on X axis and the PCR cycle number to the gene copy number on Y axis. Then, the gene copy number of the analysis sample may be appreciated by applying the fluorescence amount of the analysis sample to the standard curve.

In still another general aspect, there is provided a kit for assaying a genetically modified organism including the standard plasmid as described above.

The genetically modified organism which is the target of the kit for the assay is preferably the genetically modified corn of GM maize MON810, but the present invention is not limited thereto.

Preferably, the kit for the assay may include primer sets consisting of SEQ ID NOS: 15 and 16, and 18 and 19, and a probe consisting of SEQ ID NOS: 17 and 20, but the present invention is not limited thereto. The present invention provides the kit for assaying the genetically modified organism including the standard plasmid, thereby making it possible to perform quantitative analysis using real-time PCR for assaying the genetically modified organism containing the cry1Ab gene.

The kit may additionally include reagents for transcription, amplification, and for detecting products, and instructions therefor. For example, the kit may contain transcriptase, deoxynucleotide, thermostable polymerase which is appropriate for DNA amplification reaction and reagents for labeling and detecting nucleic acid.

In still another general aspect, there is provided a kit for assaying a genetically modified organism including protein expressed from the standard plasmid as described above. The standard plasmid of the present invention may include a T7 promoter, and the cry1Ab gene which is a transgene introduced into the standard plasmid and the ssIIb gene which is an endogene are operably linked to the T7 promoter. Therefore, Cry1Ab protein and SSIIb protein may be expressed from the standard plasmid of the present invention in suitable environment for expressing the proteins. The expressed proteins may be used as the standard protein for quantitative analysis or qualitative analysis by enzyme linked immunusorbent assay (ELISA).

Advantageous Effects

The standard plasmid according to the present invention may be utilized for assaying the genome containing the EPSPS gene, thereby being capable of determining varieties or events of the genetically modified plant. In particular, the standard plasmid is significantly useful as a standard material capable of analyzing whether the varieties such as soybean RRS is incorporated or the incorporation ratio thereof. Therefore, the present invention may provide a method for quantitatively analyzing soybean RRS which is the genetically modified organism and a kit for detecting the genetically modified organism with improved accuracy and reliability by using the standard plasmids according to the present invention, which may be very suitably utilized for accurately detecting the incorporation ratio of the genetically modified organism.

Further, the standard plasmid according to the present invention may be utilized for assaying the genome containing the cry1Ab gene, such that varieties or events of the genetically modified plant may be determined by using the standard plasmid of the present invention. In particular, the standard plasmid is significantly useful as a standard material capable of analyzing whether the varieties such as GM maize MON810 is incorporated or the incorporation ratio thereof all around the world. Therefore, the present invention may provide a method for quantitatively analyzing the genetically modified corn MON810 and a kit for detecting the genetically modified organism with improved accuracy and reliability by using the standard plasmids according to the present invention.

Further, in addition to the above-described effects, the present inventors found that the analysis method using the standard plasmid including the flanking sequence according to the present invention has remarkably improved results in view of quantitative, qualitative or economical aspects in detecting new varieties due to increase in GM varieties and hybridization between the GM varieties, particularly, in determining GM-incorporation varieties, as compared to the existing gene-specific method, and the like, and completed the present invention.

DESCRIPTION OF DRAWINGS

FIG. 17(*a*) is a schematic diagram of the existing GM's qualitative analysis, and FIG. 17(*b*) is a schematic diagram of a GM analysis method according to an exemplary embodiment of the present invention.

BEST MODE

Hereinafter, the present invention will be described in more detail with reference to exemplary embodiments of the present invention. However, it will be apparent to those skilled in the art that the following examples are only provided to illustrate the present invention and the scope of the present invention is not construed to be limited to these examples.

Example 1

1-1. Preparation of Standard Plasmid

Figure 1:
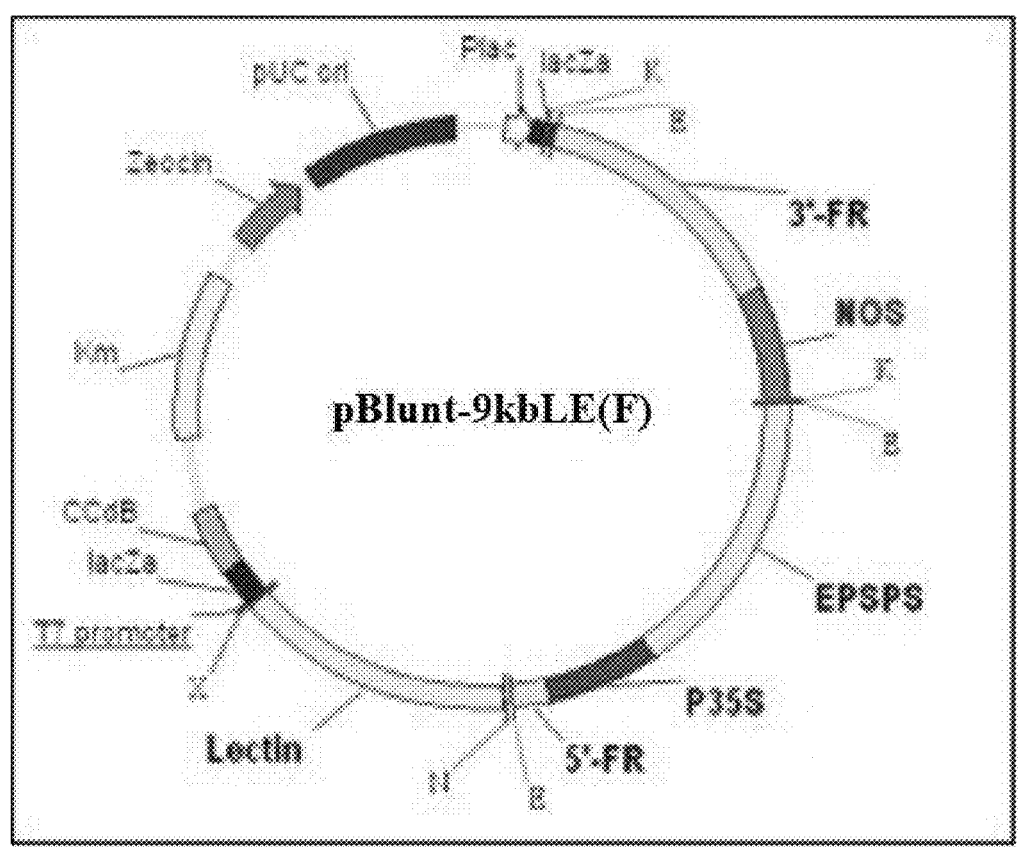
FIG. 1 shows a constitution of a standard plasmid according to an exemplary embodiment of the present invention.
Figure 3:
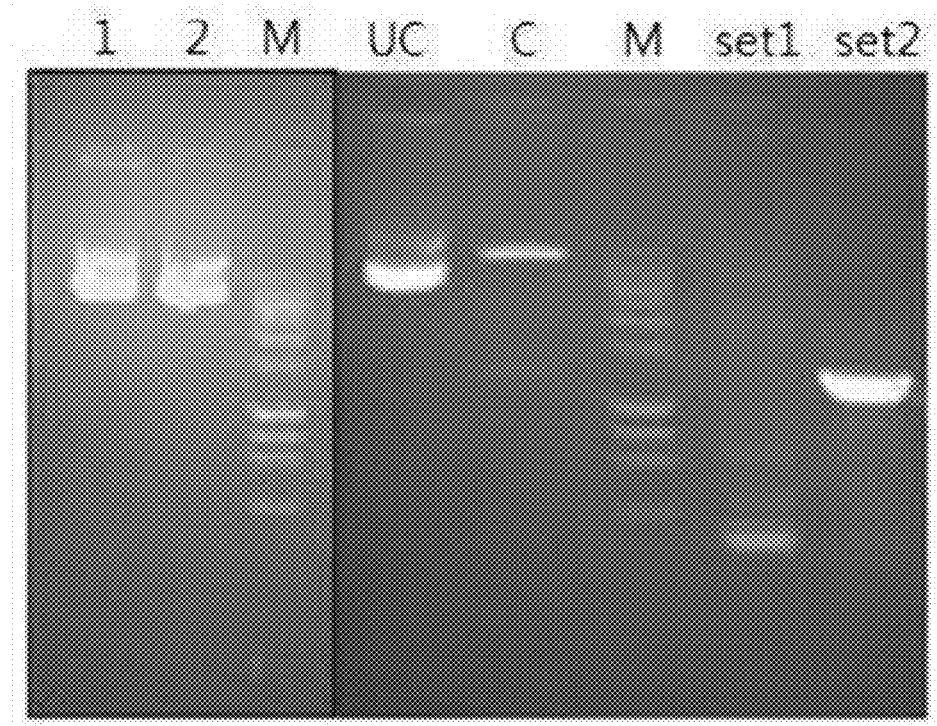
FIG. 3 is an electrophoresis image for confirming gene inserted into a vector and orientation, in order to prepare the standard plasmid according to an exemplary embodiment of the present invention. (M: Molecular weight marker; 1.2: 9kbLE pDNA; UC: plasmid DNA, C: plasmid DNA cut by enzyme, confirmation of insertion, set1 and set2: confirmation of orientation)
Figure 4:
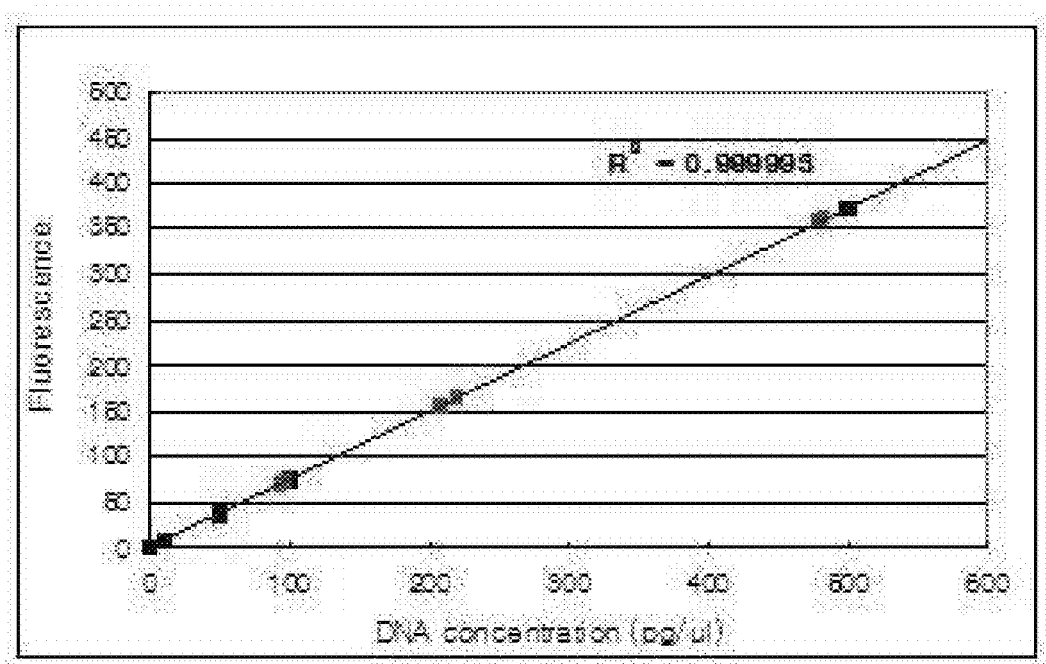
FIG. 4 is a graph showing fluorescence values of the standard plasmid DNA according to an exemplary embodiment of the present invention.

A standard plasmid was prepared by linking PCR products of an endogene (Lectin) and a GM gene (EPSPS) of soybean with each other and inserting the PCR products into a pCR-Blunt vector (Invitrogen, U.S.) (see pBlunt-9kbLE in FIG. 1). Specifically, firstly, in order to secure an insertion gene of a full gene (the flanking region is present), PCR products of the EPSPS gene amplified by a forward primer 35Sbean3F (SEQ ID NO: 11) and a reverse primer GW1R (SEQ ID NO: 12) were produced, and the PCR products were inserted into the pCR-Blunt vector. Then, in order to secure the Lectin-insertion gene, PCR products of the Lectin gene amplified by a forward primer leK1F (SEQ ID NO: 9) and a reverse primer leK1R (SEQ ID NO: 10) were produced, and treated with restriction enzymes Xba I and Not I. Then, the treated PCR products were inserted into the pCR-Blunt vector into which the EPSPS gene was inserted using Zero PCR cloning kit (Invitrogen, U.S.), thereby preparing a standard plasmid pBlunt-9kbLE. The Lectin gene inserted into the pCR-Blunt vector had a size of 1278 bp, the EPSPS gene inserted into the pCR-Blunt vector had a size of 3826 bp, and the product (insertion) which is finally inserted into the vector had a size of 5104 bp. The product (insertion) inserted into the pBlunt-9kbLE vector and the orientation thereof were confirmed as shown in FIG. 3. The recombinant plasmid pBlunt-9kbLE was introduced into *E. coli* strain TOP10 cell for transformation, and cell-cultured in an LB medium to secure a large amount of cells.

TABLE 1

| SEQ ID No: | Primer/Probe Type | Primer/Probe base sequences |
|---|---|---|
| 3 | le1n02-5' | 5'-GCCCTCTACTCCACCCCCA-3' |
| 4 | le1n02-3' | 5'-GCCCATCTGCAAGCCTTTTT-3' |
| 5 | le1-taq | 5'-FAM-AGCTTCGCCGCTTCCTTCAACTTCAC-TAMRA-3' |
| 6 | RRS 01-5' | 5'-CCTTTAGGATTTCAGCATCAGTGG-3' |
| 7 | RRS 01-3' | 5'-GACTTGTCGCCGGGAATG-3' |
| 8 | RRS-taq | 5'-TAMRA-CGCAACCGCCCGCAAATCC-TAMRA-3' |
| 9 | leK1F | 5'-CTACCCTTGTTAGTCAAACCACAC-3' |
| 10 | leK1R | 5'-CAATGACAATCACTAGCGATCGAG-3' |
| 11 | 35Sbean3F | 5'-GAACCTTGTGCAAATTATTCAAAC C-3' |
| 12 | GW1R | 5'-GTCCCCATAGATTACATAACCGAC-3' |

1-2. Plasmid DNA Extraction

Plasmid DNA (pDNA) was extracted from the large amount of cells secured in Example 1-1 by using a plasmid maxi kit (Qiagen Inc.) according to the manufacturer's guideline or with a slight modification. Specifically, the cultured cells were harvested by centrifugation (6000 g) for 15 minutes at 4° C., and the harvested cell pellet was re-suspended by adding a buffer P1 (10 ml). Next, a buffer P2 (10 ml) was added thereto, the reaction product was mixed by inverting up and down 4-6 times and allowed to stand at room temperature (15-25° C.) for 5 minutes. Then, a buffer P3 (10 ml) was added thereto, then the reaction product was mixed by inverting up and down 4-6 times and was allowed to stand on ice for 20 minutes. Then, a supernatant was centrifuged (20000 g) for 30 minutes at 4° C. (if the supernatant was not clear, the centrifugation could be additionally performed). The obtained product was equilibrated by passing a buffer QBT (10 ml) through Qiagen-tip by gravity, and the supernatant at step 5 passed through the Qiagen-tip and the Qiagen-tip was washed about twice with a buffer QC (30 ml). DNA was separated by adding a buffer QF (15 ml) to a tube (50 ml). Isopropanol (10.5 ml) was added to precipitate the separated DNA (≥15000 g) for 30 minutes at 4° C., and the supernatant was discarded. The DNA pellet of the precipitate was washed with 70% ethanol (5 ml) at room temperature, and centrifuged (≥15000 g) for 10 minutes, and the supernatant was discarded carefully. The pellet was naturally dried for 5 to 10 minutes, and dissolved in a buffer having an appropriate volume (e.g. TE buffer, pH 8.0, 10 mM Tris, pH 8.5) to prepare a finally extracted plasmid DNA (pDNA).

1-3. Confirmation of Concentration and Pollution of Plasmid DNA

Figure 2:
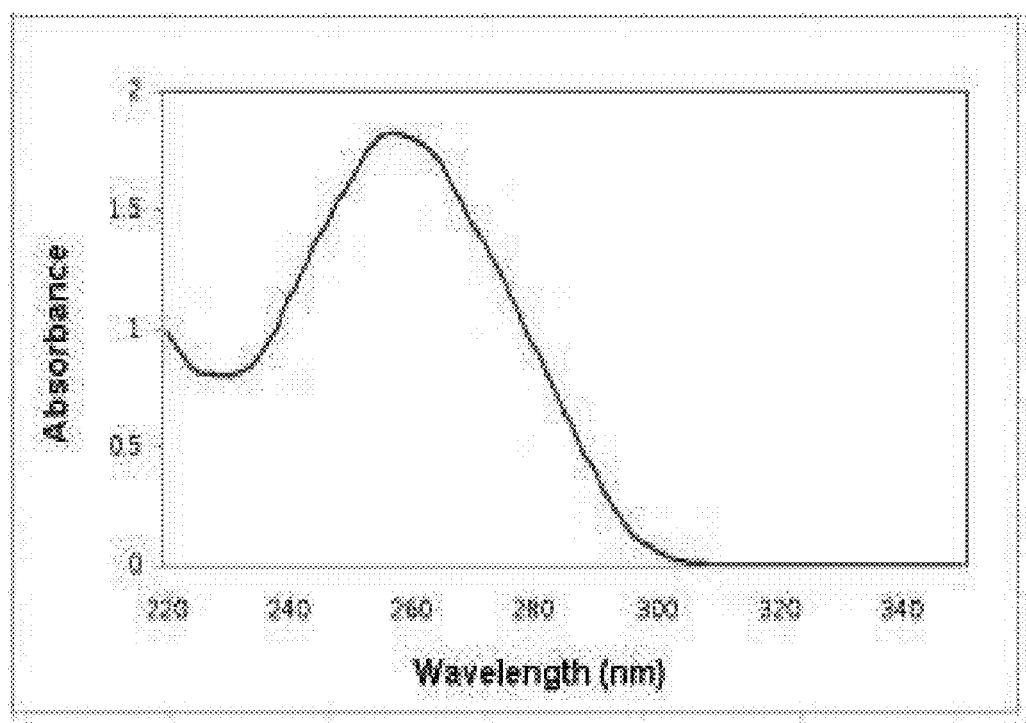
FIG. 2 is a graph showing results obtained by measuring concentration of standard plasmid DNA according to an exemplary embodiment of the present invention.

For the qualitative evaluation and quantification of the extracted plasmid DNA, absorbance measurement and fluorimetry using Pico Green™ were performed. As a result obtained by measuring UV absorbance, a DNA solution had UV absorption spectrum of a typical DNA showing peak around 260 nm (see FIG. 2 and Table 2).

Further, it was determined that the extracted plasmid DNA was a sample with good quality that has a small amount of impurities such as protein, and the like. The degree of protein pollution in the DNA solution was determined as follows. A sample in which a value obtained by dividing absorbance at 260 nm by absorbance at 280 nm is between 1.7 to 2.0 is determined as DNA with good quality having less protein pollution. It was determined that all DNA samples used in the present experiment were appropriate for the experiment since they had the value within the range. In addition, the degree of pollution of sugar (for example: polysaccharides etc., forming plant tissue) in the DNA solution could be determined by dividing absorbance at 260 nm by absorbance at 230 nm. A sample in which the value is 0.8 or more is determined as DNA with good quality. All samples used in the present experiment had a value of 0.8 or more, such that all samples were determined to have good quality with less sugar pollution for the next step (see Table 2).

TABLE 2

| Tube | 9kbLE pDNA |
|---|---|
| Undiluted Solution Concentration (ng/ul) | 451.85 |
| ⅕ Dilution Concentration (ng/ul) | 90.37 |
| 230 | 0.800 |
| 260 | 1.807 |
| 280 | 0.936 |
| Protein Incorporation (260/280) | 1.93 |
| Carbohydrate Incorporation (260/230) | 2.26 |

In order to confirm the concentration of the plasmid DNA, the amount of DNA in the solution was determined by using a method of measuring the concentration of ds-DNA (double strand DNA) using Pico Green™ (Invitrogen, Carlsbad, Calif.) which is fluorescent dye specifically bound to ds-DNA (double strand DNA). Specifically, the concentration of DNA was determined by obtaining a calibration curve with respect to the fluorescence value using a lambda DNA calibrator in which a concentration has already been known, provided in the kit, and substituting the fluorescence value of the sample into the calibration curve. As a result, the extracted plasmid DNA was confirmed to have a qualitatively appropriate purity and quantitatively sufficient concentration, and used for the next step.

1-4. Preparation of Standard Plasmid Stock

After the concentration of plasmid DNA was obtained through the fluorescence quantification, the number of copies (copy number) was calculated by substituting known plasmid DNA size (base pair: bp) to the following Equation. Then, the plasmid was diluted with 10 mM Tris so that the plasmid DNA of the final standard plasmid stock has a concentration of $4.00 \times 10^8$ cp/µl.

$$\text{Number of copies (cp/ul)} = \text{amount} \times 6.022 \times 10^{23} / \text{plasmid DNA size(bp)} \times 1 \times 10^9 \times 650$$

Impurities were removed by filtration in a clean bench, and then the obtained samples were dispensed each having an amount of 50 ul in about 900 cryo tubes (Nunc, Inc.).

In order to confirm whether the measurement values were the same as the expected number of copies, a pre-test using the real-time PCR was performed. In the present experiment, all tests were performed by using ABI 7900HT (Applied Biosystems, Inc.) and test components of basic design, primers, probes, etc., for the test, were used according to the standard of Food and Drug Administration. First, the real-time quantitative PCR was performed by using the commercially available plasmid DNA (Nippon Gene, Japan) in which the number of copies has already been known, as a standard material for preparing the standard curve, and using the plasmid DNAs extracted by Example 1-1 and Example 1-2 as analysis samples. That is, as a result obtained by amplifying endogenes for each concentration using the commercially available plasmid DNA in which the number of copies has already been known, as the standard material, it was confirmed that the interval between concentrations was regular and repetitive by adding DNA standard material among 250000, 20000, 1500, 125, 20 copies. In the GM gene, the regular and repetitive results as the same above were also confirmed.

1-5. Confirmation of Homogeneity of Standard Plasmid

Among samples dispensed in total of 900 tubes, 10 tubes were selected at a predetermined interval, and homogeneity between the tubes was confirmed.

Figure 5:
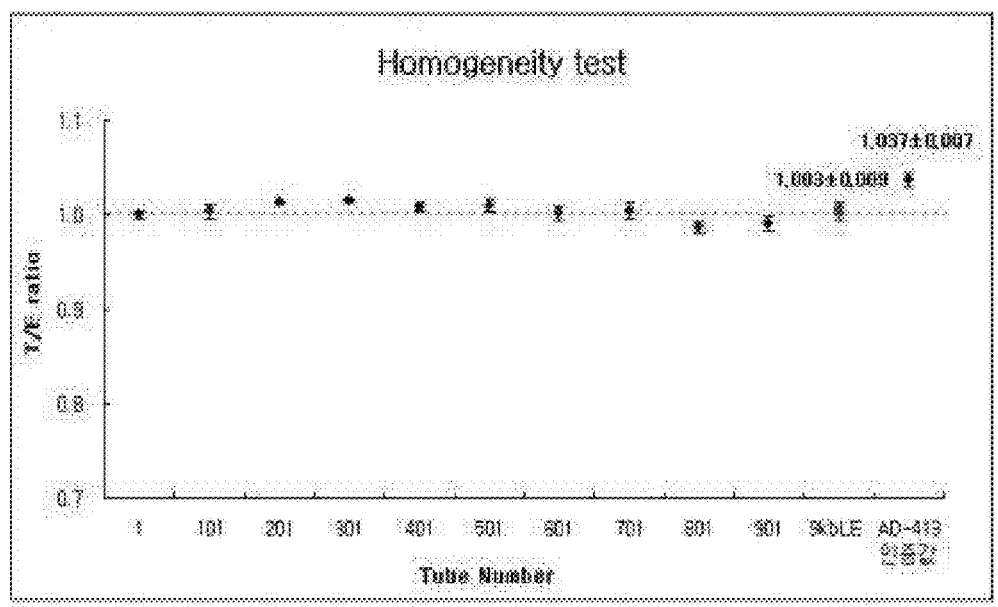
FIG. 5 shows homogeneity confirmed by performing real-time quantitative PCR using the standard plasmid DNA according to an exemplary embodiment of the present invention.

The ratios of transgene to endogene (GM gene: endogene) of the plasmid DNAs in 10 tubes analyzed to confirm homogeneity between the tubes were measured (the transgene and the endogene were genes recombined at 1:1, respectively). As a result, these measurement ratios were between 0.994 to 1.012, and an average value thereof was 1.003±0.009 (see FIG. 5). In the recombinant ERM-AD413 having the ratios of 10 tubes within in the standard deviation from each other and being prepared by IRMM, it was reported that the certified values and the range were within 1.037±0.007, which showed the homogeneity. Meanwhile, in the recombinant standard material of the present invention, the ratio between two genes was closer to 1, and accordingly, it was determined that the recombinant standard material of the present invention showed homogeneity.

1-6. Confirmation of Stability of Standard Plasmid

A test for confirming stability, which aims to confirm whether a sample is stable during transportation, was conducted by analyzing the samples of three (3) tubes at four (4) temperatures (−20° C., 4° C., room temperature and 60° C.) at predetermined time intervals (two weeks and four weeks) and observing whether there is a change in the ratio between two genes.

Figure 6:
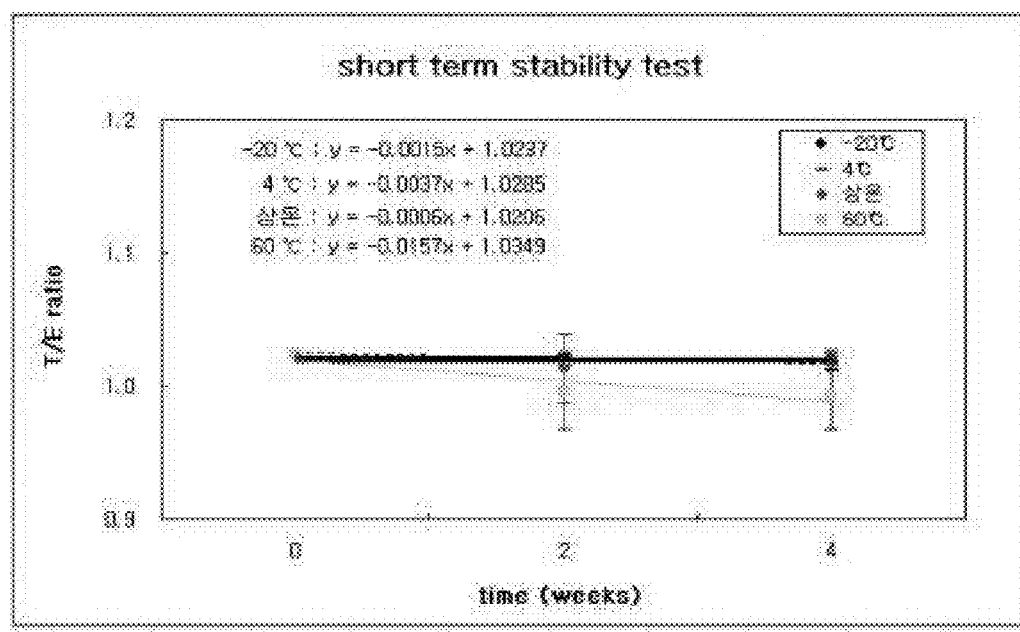
FIG. 6 shows stability confirmed by performing real-time quantitative PCR using the standard plasmid DNA according to an exemplary embodiment of the present invention.

The measurement values of ratios of transgene to endogene of the samples analyzed to confirm short-term stability were 1.023±0.001 (0 time), 1.019±0.003 (2 weeks, −20° C.), 1.020±0.007 (4 weeks, −20° C.), 1.024±0.001 (2 weeks, 4° C.), 1.016±0.004 (4 weeks, 4° C.), 1.013±0.026 (2 weeks, room temperature), 1.022±0.003 (4 weeks, room temperature), 0.996±0.028 (2 weeks, 60° C.), and 0.992±0.024 (4 weeks, 60° C.), such that the ratios of the GM gene to endogene at −20° C., 4° C., and room temperature for 4 weeks were similar to the homogeneity test results. Therefore, it could be confirmed that the samples were stable at the above temperature (see FIG. 6).

1-7. Confirmation of Quantification Using Standard Plasmid

The real-time PCR was performed by diluting the pBlunt-9kbLE plasmids with the number of copies in six (6) steps and using DNA obtained from the plasmids as a template. The obtained results were used to calculate a standard quantitative curve. Then, the quantitative analysis was performed on unknown samples. Further, a quantitative curve of the existing commercially available Nippon Gene was calculated and compared with the pBlunt-9kbLE plasmid of the present invention as a calibrator.

Figure 7A:
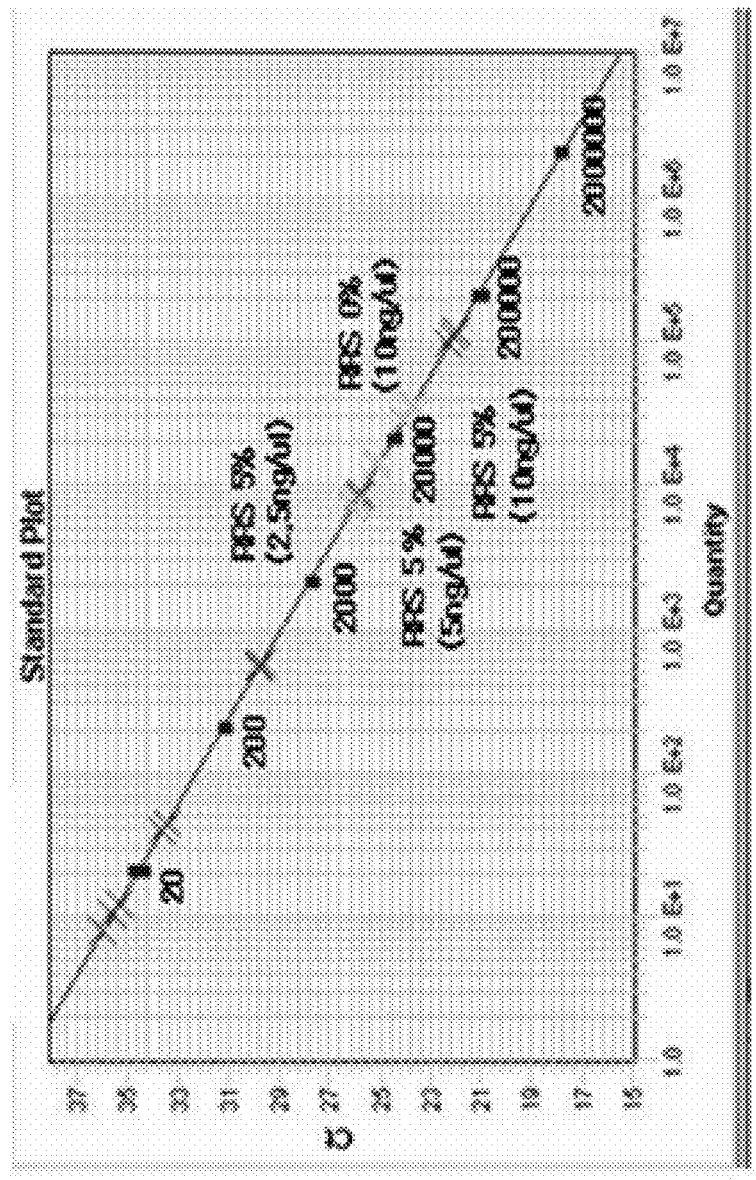
FIG. 7(a) shows quantitative analysis result of endogene in unknown sample using the standard plasmid according to an exemplary embodiment of the present invention.
Figure 7B:
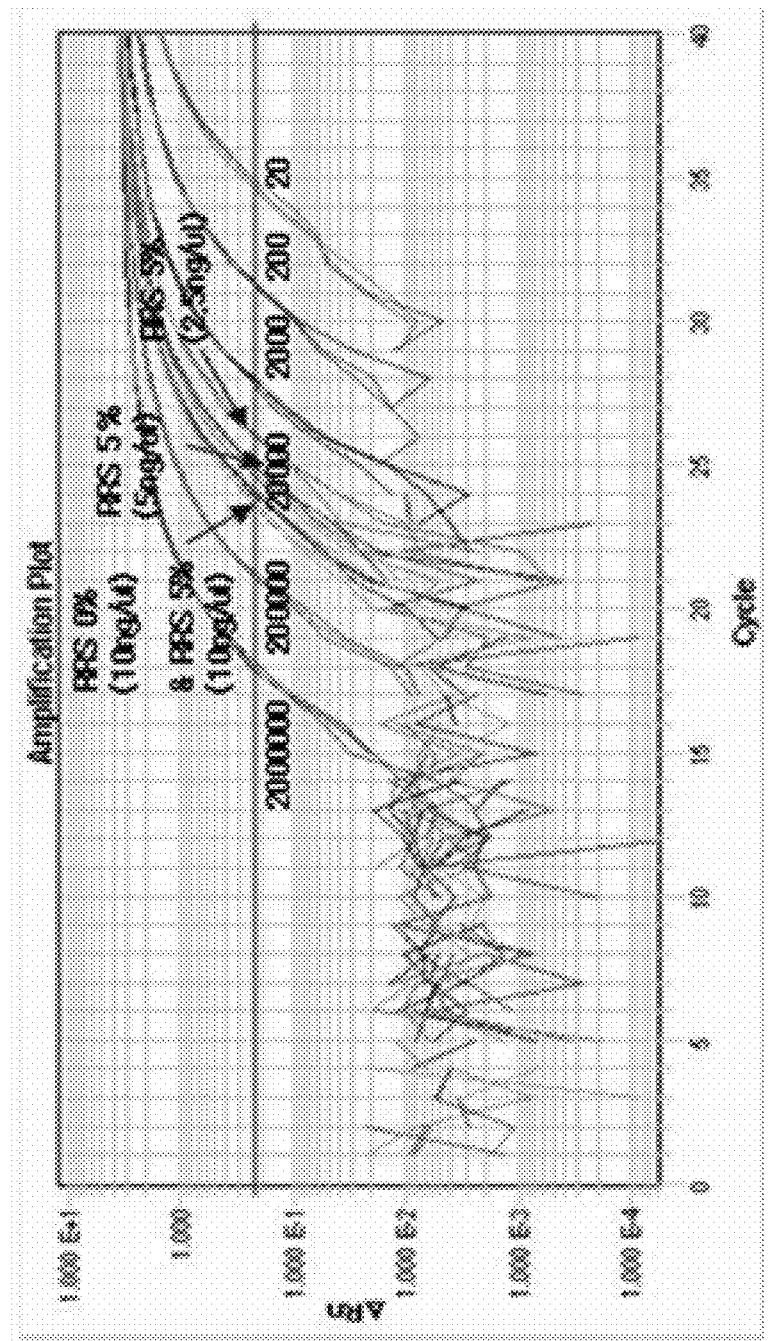
FIG. 7(b) shows real-time PCR result of the standard plasmid according to an exemplary embodiment of the present invention and the endogene in the unknown sample.
Figure 8A:
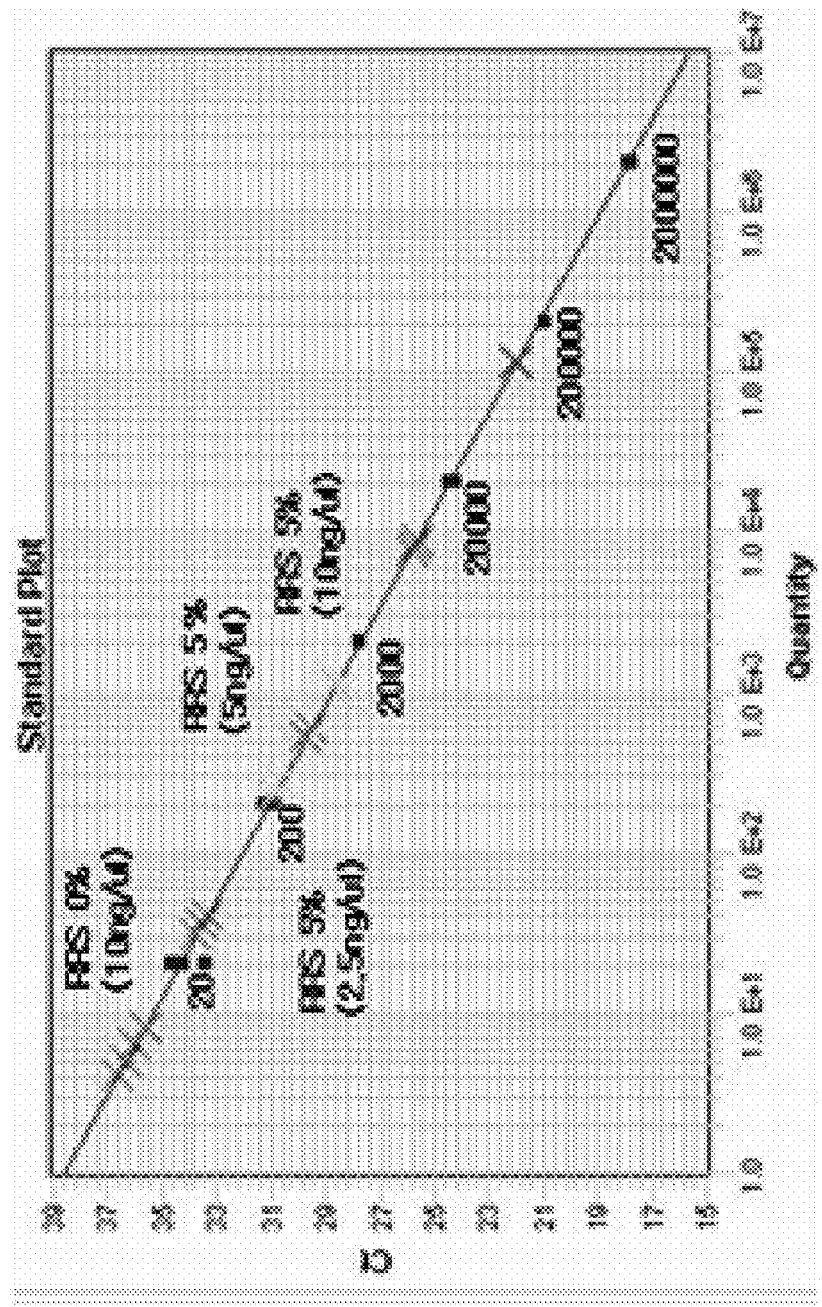
FIG. 8(a) shows quantitative analysis result of endogenes in unknown samples using the standard plasmid according to an exemplary embodiment of the present invention.
Figure 8B:
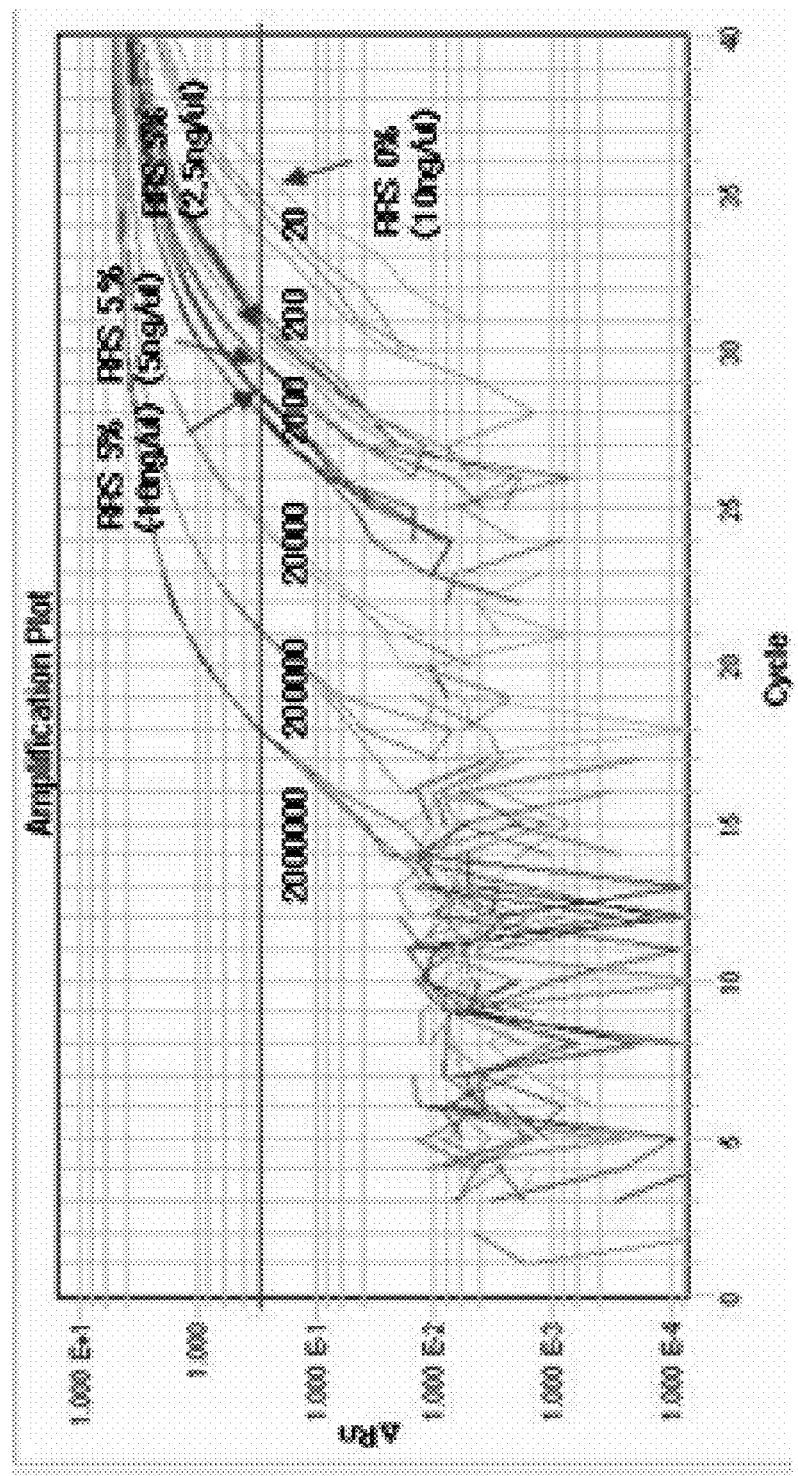
FIG. 8(b) shows real-time PCR result of the standard plasmid according to an exemplary embodiment of the present invention and the endogene in the unknown samples.

As a result, the correlation coefficients (R^2) of the pBlunt-9kbLE plasmid were 0.9996 (Lectin) and 0.9982 (EPSPS) (wherein both were 0.99 or more), which was higher than that of the Nippon Gene in which the correlation coefficients (R^2) were 0.9977 (Lectin) and 0.9980 (EPSPS), such that it could be confirmed that the plasmid according to the present invention is availably used as the standard plasmid for quantitative analysis. Further, as shown in FIGS. 7 and 8, it could be confirmed that the plasmid according to the present invention is availably used as the standard plasmid for quantitative analysis for confirming percentage (%) of the transgene (GM) in the unknown sample.

Example 2

2-1. Preparation of Standard Plasmid

Figure 9:
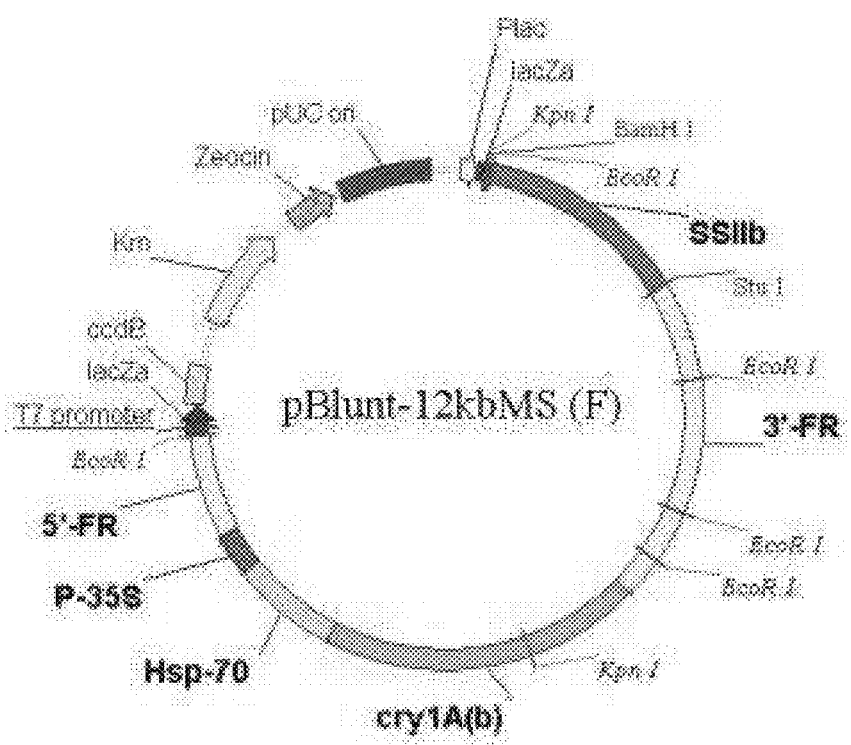
FIG. 9 shows a constitution of the standard plasmid according to an exemplary embodiment of the present invention.
Figure 11:
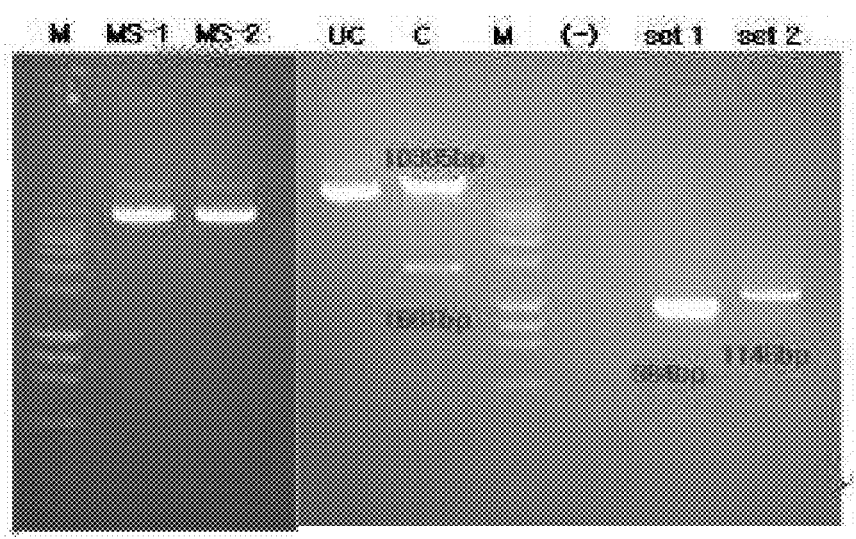
FIG. 11 is an electrophoresis image for confirming gene inserted into a vector and orientation, in order to prepare the standard plasmid according to the present invention. (M: Molecular weight marker, MS: 12bkMS, UC: plasmid DNA uncut by enzyme, C: plasmid DNA cut by enzyme, set 1: primer set for confirming ligation, set 2: primer set for confirming orientation)
Figure 12:
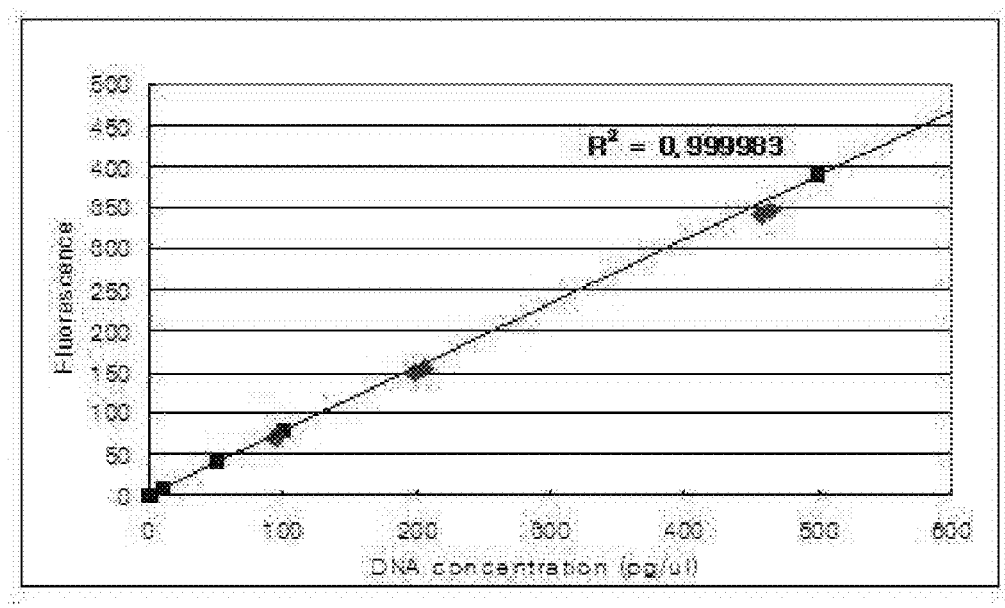
FIG. 12 is a graph showing fluorescence values of the standard plasmid DNA according to an exemplary embodiment of the present invention.

A standard plasmid was prepared by linking PCR products of an endogene (ssIIb) and a GM gene (cry1Ab) of corn with each other and inserting the PCR products into a pCR-Blunt vector (Invitrogen, U.S.) (see pBlunt-12kbMS in FIG. 9). Specifically, firstly, in order to secure an insertion gene of a full gene (the flanking region is present), PCR products of the cry1Ab gene amplified by a forward primer GWMcry3F-1 (SEQ ID NO: 23) and a reverse primer AP2 (SEQ ID NO: 24) were produced, and the PCR products were inserted into the pCR-Blunt vector. Then, in order to secure the ssIIb-insertion gene, PCR products of the ssIIb gene amplified by a forward primer SSIIb 1-5 (SEQ ID NO: 21) and a reverse primer SSIIb 2-3 (SEQ ID NO: 22) were produced, and treated with restriction enzymes BamHI and StuI. Then, the treated PCR products were inserted into the pCR-Blunt vector into which the cry1Ab gene was inserted using Zero PCR cloning kit (Invitrogen, U.S.), thereby preparing a standard plasmid pBlunt-12kbMS. The ssIIb gene inserted into the pCR-Blunt vector had a size of 1622 bp, the cry1Ab gene inserted into the pCR-Blunt vector had a size of 6922 bp, and the product (insertion) which is finally inserted into the vector had a size of 8544 bp. The product (insertion) inserted into the pBlunt-12kbMS vector and the orientation thereof were confirmed as shown in FIG. 11. The recombinant plasmid pBlunt-12kbMS was introduced into *E. coli* strain TOP10 cell for transformation, and cell-cultured in an LB medium for mass-production.

TABLE 3

| SEQ ID No: | Primer/Probe Type | Primer/Probe base sequences |
|---|---|---|
| 15 | SSIIb 5' | 5'-CTC CCA ATC CTT TGA CAT CTG C-3' |
| 16 | SSIIb 3' | 5'-TCG ATT TCT CTC TTG GTG ACA GG-3' |
| 17 | SSIIb-taq | 5'-FAM-AGC AAA GTC AGA GCG CTG CAA TGC A-TAMRA-3' |
| 18 | MON810 5' | 5'-GAT GCC TTC TCC CTA GTG TTG A-3' |
| 19 | MON810 3' | 5'-GGA TGC ACT CGT TGA TGT TTG-3' |
| 20 | MON810-taq | 5'-FAM-AGA TAC CAA GCG GCC ATG GAC AAC AA-TAMRA-3' |
| 21 | SSIIb 1-5 | 5'-CTC CCA ATC CTT TGA CAT CTG C-3' |
| 22 | SSIIb 2-3 | 5'-GAC TTG CCT GAA CAC TAC ATC GAC-3' |
| 23 | GWMcry3F-1 | 5'-GAC GTT CTC AGA GAC AGT ATT CAA CTT TG-3' |
| 24 | AP2 | 5'-ACT ATA GGG CAC GCG TGG T-3' |

2-2. Plasmid DNA Extraction

Plasmid DNA (pDNA) was extracted from the large amount of cells secured in Example 2-1 by using a plasmid maxi kit (Qiagen Inc.) according to the manufacturer's guideline or with a slight modification. Specifically, the cultured cells were harvested by centrifugation (6000 g) for 15 minutes at 4° C., and the harvested cell pellet was re-suspended by adding a buffer P1 (10 ml). Next, a buffer P2 (10 ml) was added thereto, then the reaction product was mixed by inverting up and down 4-6 times and was allowed to stand at room temperature (15-25° C.) for 5 minutes. Then, a buffer P3 (10 ml) was added thereto, the reaction product was mixed by inverting up and down 4-6 times and allowed to stand on ice for 20 minutes. Then, a supernatant was centrifuged (20000 g) for 30 minutes at 4° C. (if the supernatant was not clear, the centrifugation could be additionally performed). The obtained product was equilibrated by passing a buffer QBT (10 ml) through Qiagen-tip by gravity, and the supernatant at step 5 passed through the Qiagen-tip and the Qiagen-tip was washed twice with a buffer QC (30 ml). DNA was separated by adding a buffer QF (15 ml) to a tube (50 ml). Isopropanol (10.5 ml) was added to precipitate the separated DNA (15000 g) for 30 minutes at 4° C., and the supernatant was discarded. The DNA pellet of the precipitate was washed with 70% ethanol (5 ml) at room temperature, and centrifuged (15000 g) for 10 minutes, and the supernatant was discarded carefully. The pellet was naturally dried for 5 to 10 minutes, and dissolved in a buffer having an appropriate volume (e.g. TE buffer, pH 8.0, 10 mM Tris, pH 8.5) to prepare a finally extracted plasmid DNA (pDNA).

2-3. Confirmation of Concentration and Pollution of Plasmid DNA

Figure 10:
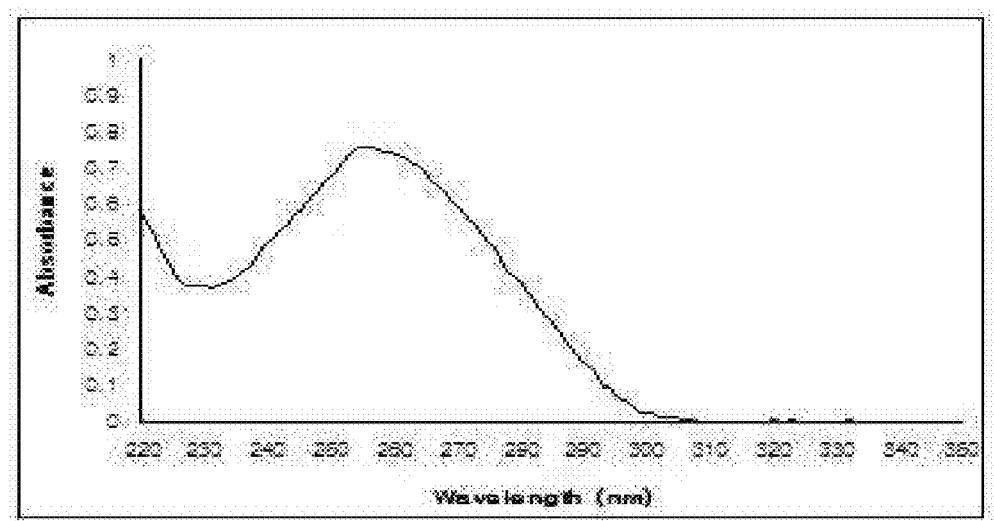
FIG. 10 is a graph showing results obtained by measuring concentration of the standard plasmid DNA according to an exemplary embodiment of the present invention.

For the qualitative evaluation and quantification of the extracted plasmid DNA, absorbance measurement and fluorimetry using Pico Green™ were performed. As a result obtained by measuring UV absorbance, a DNA solution had UV absorption spectrum of a typical DNA showing peak around 260 nm (see FIG. 10 and Table 4).

Further, it was determined that the extracted plasmid DNA was a sample with good quality that has a small amount of impurities such as protein, and the like. The degree of protein pollution in the DNA solution was determined as follows. A sample in which a value obtained by dividing absorbance at 260 nm by absorbance at 280 nm is between 1.7 to 2.0 is determined as DNA with good quality having less protein pollution. It was determined that all DNA samples used in the present experiment were appropriate for the experiment since they had the value within the range. In addition, the degree of pollution of sugar (for example: polysaccharides etc., forming plant tissue) in the DNA solution could be determined by dividing absorbance at 260 nm by absorbance at 230 nm. A sample in which the value is 0.8 or more is determined as DNA with good quality. All DNA samples used in the present experiment had a value of 0.8 or more, such that all samples were determined to have good quality with less sugar pollution for the next step (see Table 4).

TABLE 4

| Tube | 12kbMS |
|---|---|
| Undiluted Solution Concentration (ng/ul) | 175.55 |
| 1/5 Dilution Concentration (ng/ul) | 35.11 |
| 230 | 0.333 |
| 260 | 0.702 |
| 280 | 0.371 |
| Protein Incorporation (260/280) | 1.89 |
| Carbohydrate Incorporation (260/230) | 2.11 |

In order to confirm the concentration of the plasmid DNA, the amount of DNA in the solution was determined by using a method of measuring the concentration of ds-DNA (double strand DNA) using Pico Green™ (Invitrogen, Carlsbad, Calif.) which is fluorescent dye specifically bound to ds-DNA (double strand DNA). Specifically, the concentration of DNA was determined by obtaining a calibration curve with respect to the fluorescence value using a lambda DNA calibrator in which a concentration has already been known, provided in the kit, and substituting the fluorescence value of the sample into the calibration curve. As a result, the extracted plasmid DNA was confirmed to have a qualitatively appropriate purity and quantitatively sufficient concentration, and used for the next step.

2-4. Preparation of Standard Plasmid Stock

After the concentration of plasmid DNA was obtained through the fluorescence quantification, the number of copies (copy number) was calculated by substituting known plasmid DNA size (base pair: bp) to the following Equation. Then, the plasmid was diluted with 10 mM Tris so that the final plasmid stock has a concentration of $4.00 \times 10^8$ cp/μl.

Number of copies (cp/ul)=amount$\times 6.022 \times 10^{23}$/plasmid DNA size (bp)$\times 1 \times 10^9 \times 650$ Impurities were removed by filtration in a clean bench, and then the obtained samples were dispensed each having an amount of 50 ul in about 800 cryo tubes (Nunc, Inc.).

In order to confirm whether the measurement values were the same as the expected number of copies, a pre-test using the real-time PCR was performed. In the present experiment, all tests were performed by using ABI 7900HT (Applied Biosystems, Inc.) and a basic design for the test and test components such as primers, probes, etc., for the test, were used according to the standard of Food and Drug Administration. First, the real-time quantitative PCR was performed by using the commercially available plasmid DNA (Nippon Gene, Japan) in which the number of copies has already been known, as a standard material for preparing the standard curve, and using the plasmid DNAs extracted by Example 2-1 and Example 2-2 as analysis samples. As a result obtained by amplifying endogenes for each concentration using the commercially available plasmid DNA in which the number of copies has already been known, as the standard material, it was confirmed that the interval between concentrations was regular and repetitive by adding DNA standard material among 250000, 20000, 1500, 125, and 20 copies. In the GM gene, the regular and repetitive results as the same above were also confirmed.

2-5. Confirmation of Homogeneity of Standard Plasmid

Among samples dispensed in total of 800 tubes, 10 tubes were selected at a predetermined interval, and homogeneity between the tubes was confirmed.

Figure 13:
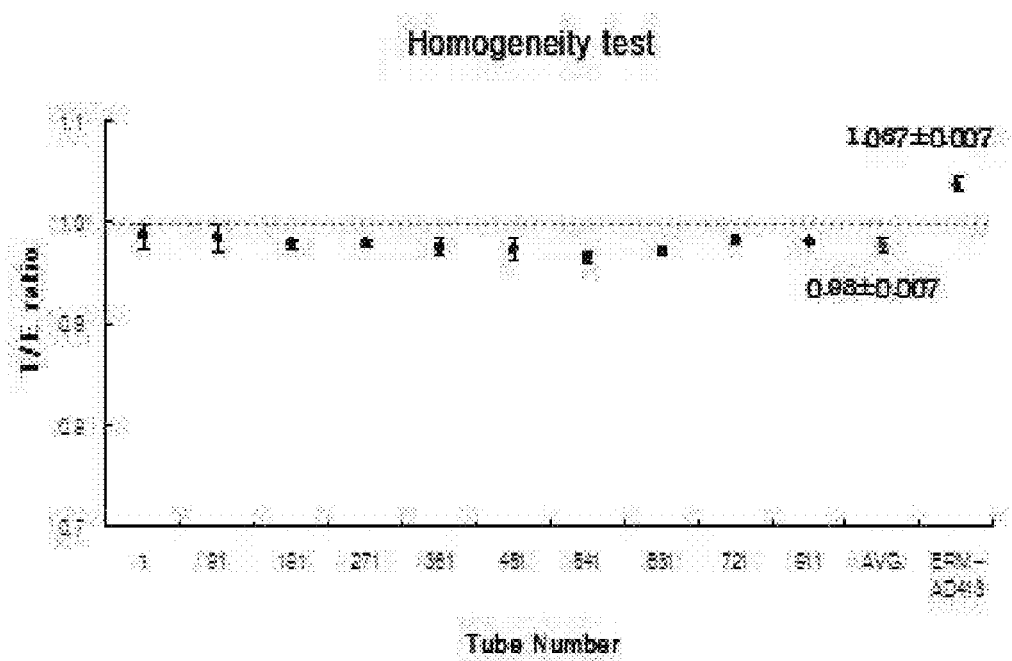
FIG. 13 shows homogeneity confirmed by performing real-time quantitative PCR using the standard plasmid DNA according to an exemplary embodiment of the present invention.

The ratios of transgene to endogene (GM gene: endogene) of the plasmid DNAs in 10 tubes analyzed to confirm homogeneity between the tubes were measured (the transgene and the endogene were genes recombined at 1:1, respectively). As a result, these measurement ratios were between 0.971 to 0.985, and an average value thereof was 0.98±0.007 (see FIG. 13). In the recombinant ERM-AD413 having the ratios of 10 tubes within the standard deviation from each other and being prepared by IRMM, it was reported that the certified values and the range were within 1.037±0.007, which showed the homogeneity. Meanwhile, in the recombinant standard material of the present invention, the ratio between two genes was closer to 1, and accordingly, it was determined that the recombinant standard material of the present invention showed homogeneity.

2-6. Confirmation of Stability of Standard Plasmid

A test for confirming stability, which aims to confirm whether a sample is stable during transportation, was conducted by analyzing the samples of three (3) tubes at four (4) temperatures (−20° C., 4° C., room temperature and 60° C.) at predetermined time intervals (two weeks and four weeks) and observing whether there is a change in the ratio between two genes.

Figure 14:
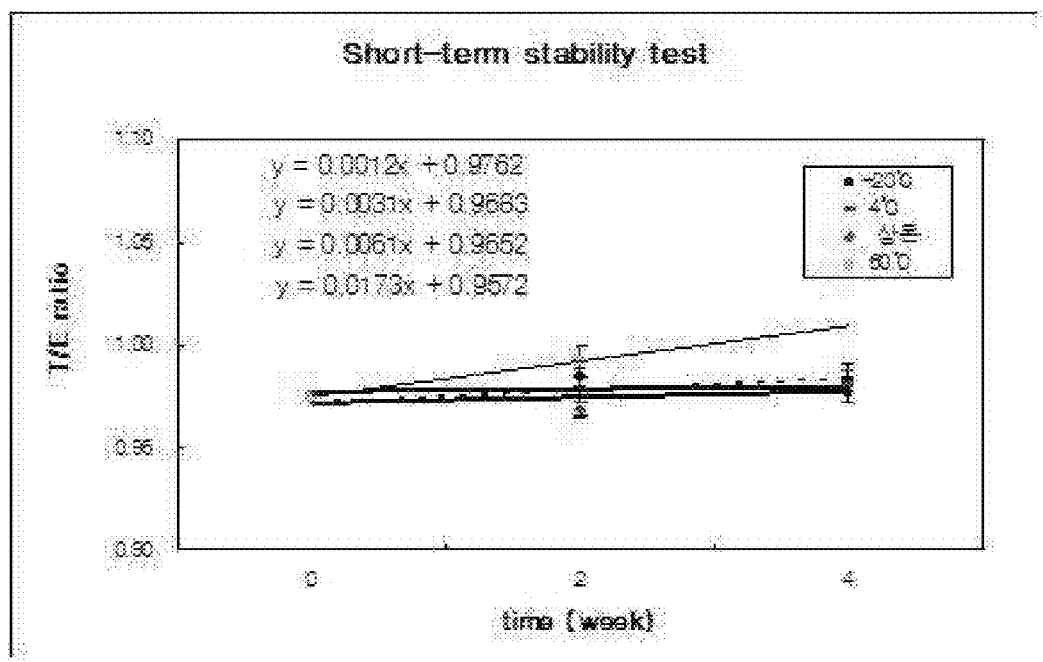
FIG. 14 shows stability confirmed by performing real-time quantitative PCR using the standard plasmid DNA according to an exemplary embodiment of the present invention.

The measurement values of ratios of transgene to endogene of the samples analyzed to confirm short-term stability were 0.974±0.002 (0 time), 0.984±0.005 (2 weeks, −20° C.), 0.980±0.011 (4 weeks, −20° C.), 0.971±0.006 (2 weeks, 4° C.), 0.987±0.004 (4 weeks, 4° C.), 0.968±0.004 (2 weeks, room temperature), 0.973±0.012 (4 weeks, room temperature), and 0.992±0.008 (2 weeks, 60° C.), such that the ratios of the GM gene to endogene at −20° C., 4° C., and room temperature for 4 weeks were similar to the homogeneity test results. Therefore, it could be confirmed that the samples were stable at the above temperature (see FIG. 14).

2-7. Confirmation of Quantification Using Standard Plasmid

The real-time PCR was performed by diluting the pBlunt-12kbMS plasmids with the number of copies in six (6) steps and using DNA obtained from the plasmids as a template.

Figure 15A:
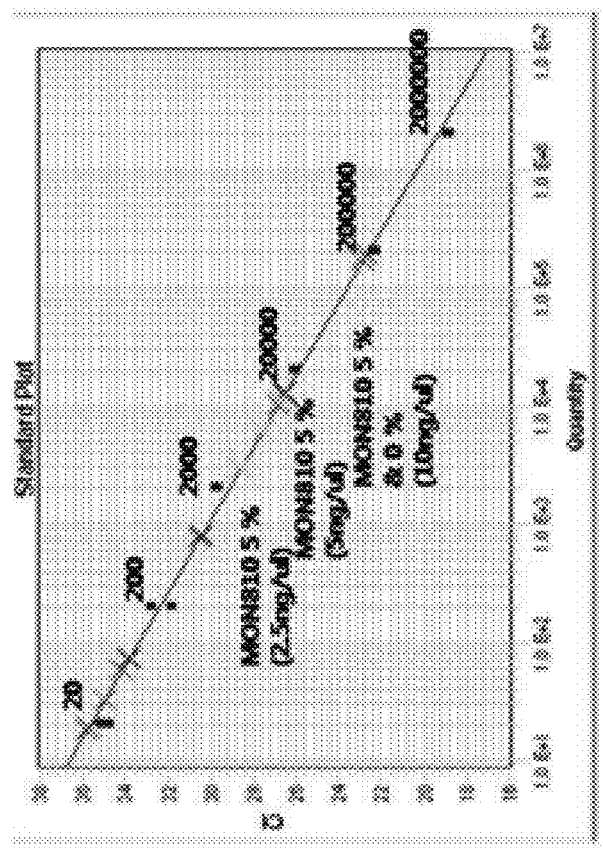
FIG. 15(*a*) shows quantitative analysis result of endogenes in unknown samples using the standard plasmid according to an exemplary embodiment of the present invention, and FIG. 15(*b*) shows real-time PCR result of the standard plasmid according to an exemplary embodiment of the present invention and the endogene in the unknown samples.
Figure 15B:
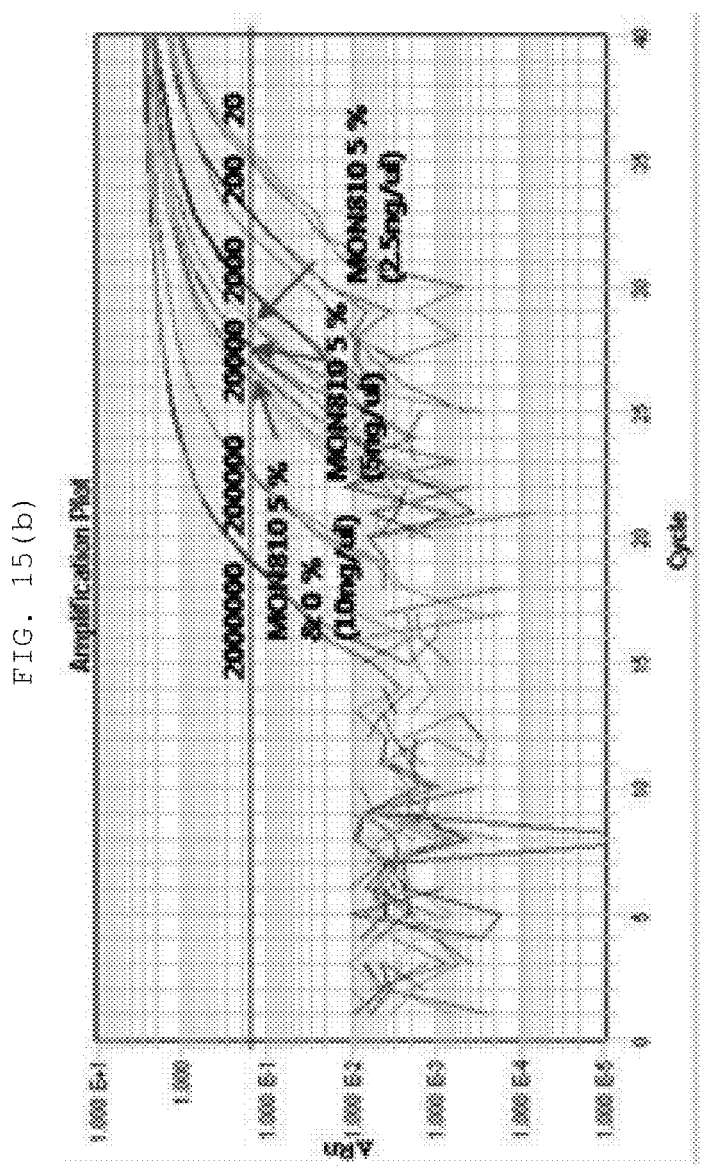
Figure 16A:
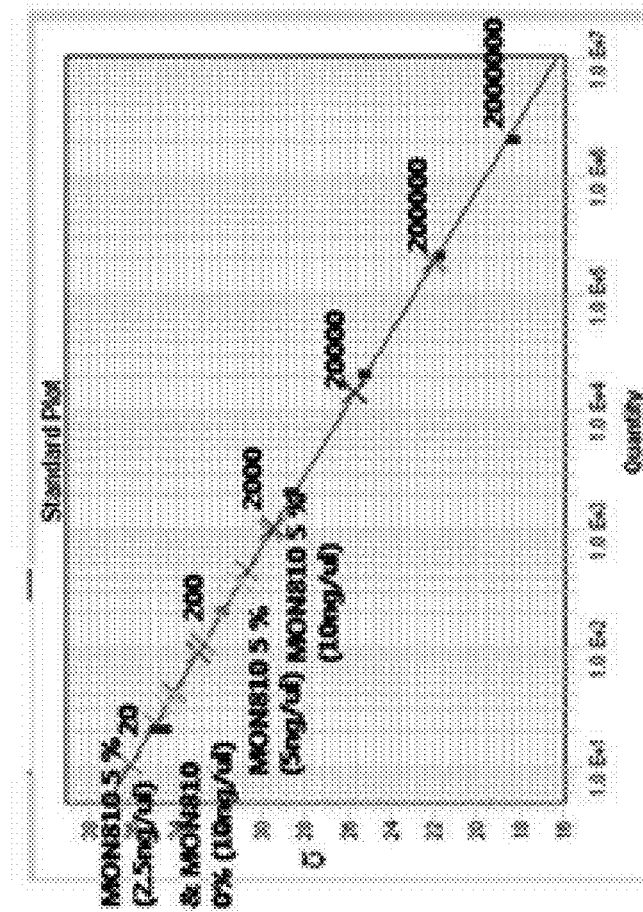
FIG. 16(*a*) shows quantitative analysis result of transgenes in unknown samples using the standard plasmid according to the present invention, and FIG. 16(*b*) shows real-time PCR result of the standard plasmid according to the present invention and the transgene in the unknown samples.
Figure 16B:
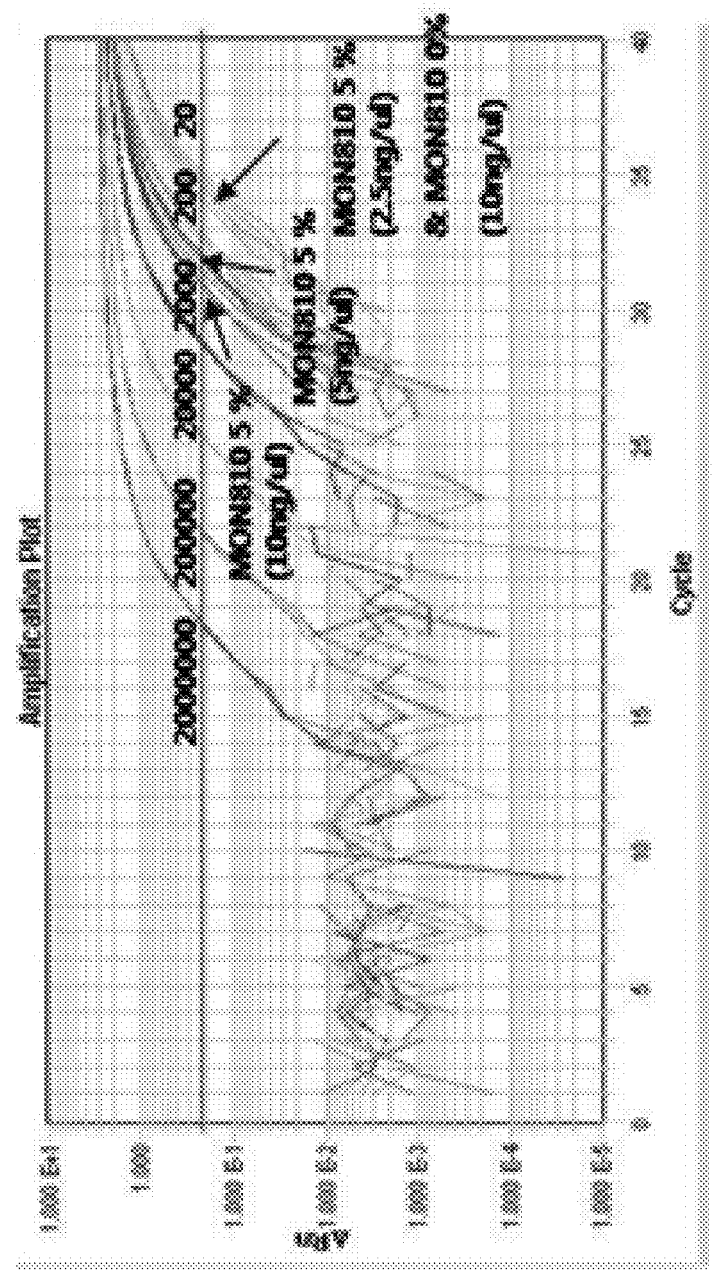

The obtained results were used to calculate a standard quantitative curve. Then, the quantitative analysis was performed on unknown samples. Further, a quantitative curve of the existing commercially available Nippon Gene was calculated and compared with the pBlunt-12kbMS plasmid of the present invention as a calibrator. As a result, the correlation coefficients ($R^2$) of the pBlunt-12kbMS plasmid were 0.9933 (ssIIb) and 0.9985 (cry1Ab) (wherein both were 0.99 or more), which was higher than that of the Nippon Gene in which the correlation coefficients ($R^2$) were 0.9923 (ssIIb) and 0.9923 (cry1Ab), such that it could be confirmed that the plasmid according to the present invention is availably used as the standard plasmid for quantitative analysis. Further, as shown in FIGS. 15 and 16, it could be confirmed that the plasmid according to the present invention is availably used as the standard plasmid for quantitative analysis for confirming percentage (%) of the transgene (GM) in the unknown sample.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

[Sequence Listing Free Text]

Sequence Listing is attached as a separate file.

The invention claimed is:

1. A standard plasmid for assaying a genetically modified organism, said standard plasmid comprising:
   a ssIIb gene and a cry1Ab gene.

2. The standard plasmid of claim 1, wherein the cry1Ab gene includes a 5' flanking sequence and a 3' flanking sequence.

3. The standard plasmid of claim 1, wherein, the cry1Ab gene includes the base sequence of SEQ ID NO: 13, and the ssIIb gene includes the base sequence of SEQ ID NO: 14.

4. The standard plasmid of claim 1, wherein the genetically modified organism is a GM maize MON810.

5. A method for quantitatively analyzing a target transgene within a genetically modified plant using the standard plasmid of claim 1, comprising:
   i) preparing a series of dilutions of said standard plasmid;
   ii) performing a real-time PCR on the dilutions of the standard plasmid and a DNA sample of the genetically modified plant, respectively, using a PCR primer set and a probe which bind to the target transgene and the standard plasmid;
   iii) providing a standard quantitative curve from measured amounts of PCR products obtained in step ii) by using the dilutions of the standard plasmid; and
   iv) determining an incorporation ratio of the target transgene by comparing the measured amounts of PCR products obtained from the DNA of the generically modified plant, with the standard quantitative curve provided in step iii).

6. The method of claim 5, wherein the genetically modified plant is GM maize MON810.

7. The method of claim 5, wherein in step ii), the PCR primer sets are a primer set of SEQ ID NOS: 15 and 16 and a primer set of SEQ ID NOS: 18 and 19, and the probe consists of SEQ ID NOS: 17 and 20.

8. A kit for assaying a genetically modified organism, said kit comprising the standard plasmid of claim 1.

9. The kit of claim 8, wherein the kit includes:
   primer sets consisting of SEQ ID NOS: 15 and 16, and SEQ ID NOS: 18 and 19, and
   a probe consisting of SEQ ID NOS: 17 and 20.

* * * * *